(12) United States Patent
Learn

(10) Patent No.: US 11,478,325 B2
(45) Date of Patent: Oct. 25, 2022

(54) LIGHTING APPARATUS

(71) Applicant: Clifton Learn, La Jolla, CA (US)

(72) Inventor: Clifton Learn, La Jolla, CA (US)

(\*) Notice: Subject to any disclaimer, the term of this patent is extended or adjusted under 35 U.S.C. 154(b) by 0 days.

(21) Appl. No.: 17/098,557

(22) Filed: Nov. 16, 2020

(65) Prior Publication Data

US 2021/0077219 A1 Mar. 18, 2021

Related U.S. Application Data

(63) Continuation of application No. 15/502,078, filed as application No. PCT/US2015/043977 on Aug. 6, 2015, now Pat. No. 10,869,733.

(Continued)

(51) Int. Cl.
*F21V 33/00* (2006.01)
*A61B 90/30* (2016.01)
(Continued)

(52) U.S. Cl.
CPC .............. *A61B 90/30* (2016.02); *A41D 1/002* (2013.01); *A41D 13/0025* (2013.01); *A41D 20/005* (2013.01); *A61B 90/50* (2016.02); *F21L 4/00* (2013.01); *F21L 4/04* (2013.01); *F21V 14/065* (2013.01); *F21V 15/01* (2013.01); *F21V 17/164* (2013.01); *F21V 23/0414* (2013.01);
(Continued)

(58) Field of Classification Search
CPC . A61B 90/35; A61B 2090/502; F21V 21/084; F21V 29/67; F21V 29/673; F21V 29/677; F21V 33/0096
See application file for complete search history.

(56) References Cited

U.S. PATENT DOCUMENTS 3,371,202 A  2/1968 Moore et al.
3,875,397 A  4/1975 Nicholl
(Continued)

FOREIGN PATENT DOCUMENTS

CN  201651790 U  11/2010
DE  102010047477 B4  2/2014
(Continued)

OTHER PUBLICATIONS

International Search Report and Written Opinion for: PCT/US2015/043977 dated Jan. 7, 2016.
(Continued)

*Primary Examiner* — Sean P Gramling
(74) *Attorney, Agent, or Firm* — Hansen IP Law PLLC

(57) ABSTRACT

A lighting apparatus for use as a surgical headlamp is disclosed. A light emitting diode is positioned in a recess within a frustoconical, thermally-conductive heat sink that has a several circumferential ridges to provide a desired surface area for heat transfer. The diode and the heat sink are provided in a housing that also includes a fan for drawing ambient air into the housing to contact the heat sink and exhausting heated air. A lens is snap-fit into a slide that frictionally engages the interior of the housing, allowing a user to adjust the spacing between the light emitting diode and the lens as desired. Personal cooling apparatuses usable with the lighting apparatus are also described. Auxiliary undergown switches are also described as are personal cooling apparatuses.

18 Claims, 20 Drawing Sheets

Related U.S. Application Data

(60) Provisional application No. 62/034,867, filed on Aug. 8, 2014.

(51) Int. Cl.

| | | |
|---|---|---|
| *F21L 4/04* | (2006.01) | |
| *F21V 29/76* | (2015.01) | |
| *F21V 14/06* | (2006.01) | |
| *F21V 29/67* | (2015.01) | |
| *F21V 29/77* | (2015.01) | |
| *A61B 90/50* | (2016.01) | |
| *A41D 1/00* | (2018.01) | |
| *A41D 13/002* | (2006.01) | |
| *A41D 20/00* | (2006.01) | |
| *F21L 4/00* | (2006.01) | |
| *F21V 15/01* | (2006.01) | |
| *F21V 17/16* | (2006.01) | |
| *F21V 23/04* | (2006.01) | |
| *H01M 10/48* | (2006.01) | |
| *F21V 29/89* | (2015.01) | |
| *F21Y 115/10* | (2016.01) | |

(52) U.S. Cl.
CPC .......... *F21V 29/673* (2015.01); *F21V 29/767* (2015.01); *F21V 29/773* (2015.01); *H01M 10/482* (2013.01); *H01M 10/488* (2013.01); *A61B 2090/502* (2016.02); *F21V 29/89* (2015.01); *F21Y 2115/10* (2016.08); *H01M 2220/30* (2013.01)

(56) References Cited

U.S. PATENT DOCUMENTS

| | | | |
|---|---|---|---|
| 4,672,968 A * | 6/1987 | Lenox | A41D 13/1209 |
| | | | 2/171.3 |
| 4,681,413 A | 7/1987 | Schmidt et al. | |
| 5,440,462 A | 8/1995 | Kim et al. | |
| 6,908,208 B1 * | 6/2005 | Hyde | F21V 33/0096 |
| | | | 362/108 |
| 7,210,810 B1 | 5/2007 | Iversen et al. | |
| 7,441,282 B2 | 10/2008 | Heine et al. | |
| 7,465,078 B2 | 12/2008 | Chang | |
| 7,690,806 B2 | 4/2010 | Feinbloom et al. | |
| 7,871,174 B2 | 1/2011 | Heine et al. | |
| 7,883,233 B2 | 2/2011 | Feinbloom et al. | |
| 8,047,684 B2 | 11/2011 | Chang | |
| 8,215,791 B2 | 7/2012 | Feinbloom et al. | |
| 8,348,448 B2 | 1/2013 | Orozco et al. | |
| 8,534,861 B2 | 9/2013 | Leegate et al. | |
| 8,899,744 B2 | 12/2014 | Strong et al. | |
| 2005/0207148 A1 | 9/2005 | Maglica | |
| 2005/0207161 A1 | 9/2005 | Romano et al. | |
| 2006/0072310 A1 | 4/2006 | Hung | |
| 2006/0145180 A1 | 7/2006 | Galli | |
| 2006/0250771 A1 | 11/2006 | Heine et al. | |
| 2007/0097702 A1 | 5/2007 | Crowder | |
| 2007/0097703 A1 | 5/2007 | Goldfain | |
| 2008/0055893 A1 | 3/2008 | Au et al. | |
| 2009/0016045 A1 | 1/2009 | Medinis | |
| 2009/0303698 A1 | 12/2009 | Huss et al. | |
| 2011/0026258 A1 | 2/2011 | Chang | |
| 2011/0105851 A1 | 5/2011 | Horvath | |
| 2011/0199755 A1 | 8/2011 | Falk et al. | |
| 2012/0099308 A1 | 4/2012 | Brukilacchio | |
| 2012/0120635 A1 * | 5/2012 | Strong | F21V 5/008 |
| | | | 362/105 |
| 2012/0162993 A1 | 6/2012 | Cheng et al. | |
| 2012/0275140 A1 | 11/2012 | Feinbloom et al. | |
| 2012/0320454 A1 | 12/2012 | Chang | |
| 2012/0320568 A1 | 12/2012 | Chang | |
| 2013/0301254 A1 | 11/2013 | Popper et al. | |
| 2013/0329409 A1 | 12/2013 | Windom | |
| 2014/0139344 A1 | 5/2014 | Chudy | |
| 2015/0073227 A1 | 3/2015 | Teder et al. | |

FOREIGN PATENT DOCUMENTS

| | | |
|---|---|---|
| EP | 3177865 B2 | 12/2019 |
| EP | 3657065 A1 | 5/2020 |
| GB | 2504686 A | 2/2014 |
| WO | 2016022777 A1 | 2/2016 |

OTHER PUBLICATIONS

English translation of DE 10 2010 047 477 from Lexis Nexis Total Patent.
Extended European Search Report for EP Patent App. No. 15 830 677.9 dated Jan. 8, 2018.
European Patent Office (EPO) Communication pursuant to rules 70(2) and 70a(2) EPC25, 2018 for EP Patent App. No. 15 830 677.9 dated Jan. 25, 2018.
Extended European Search Report dated Apr. 21, 2020 for EP 19213753.7.

* cited by examiner

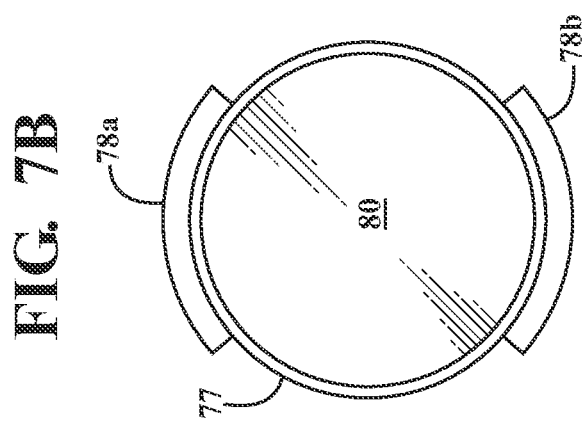
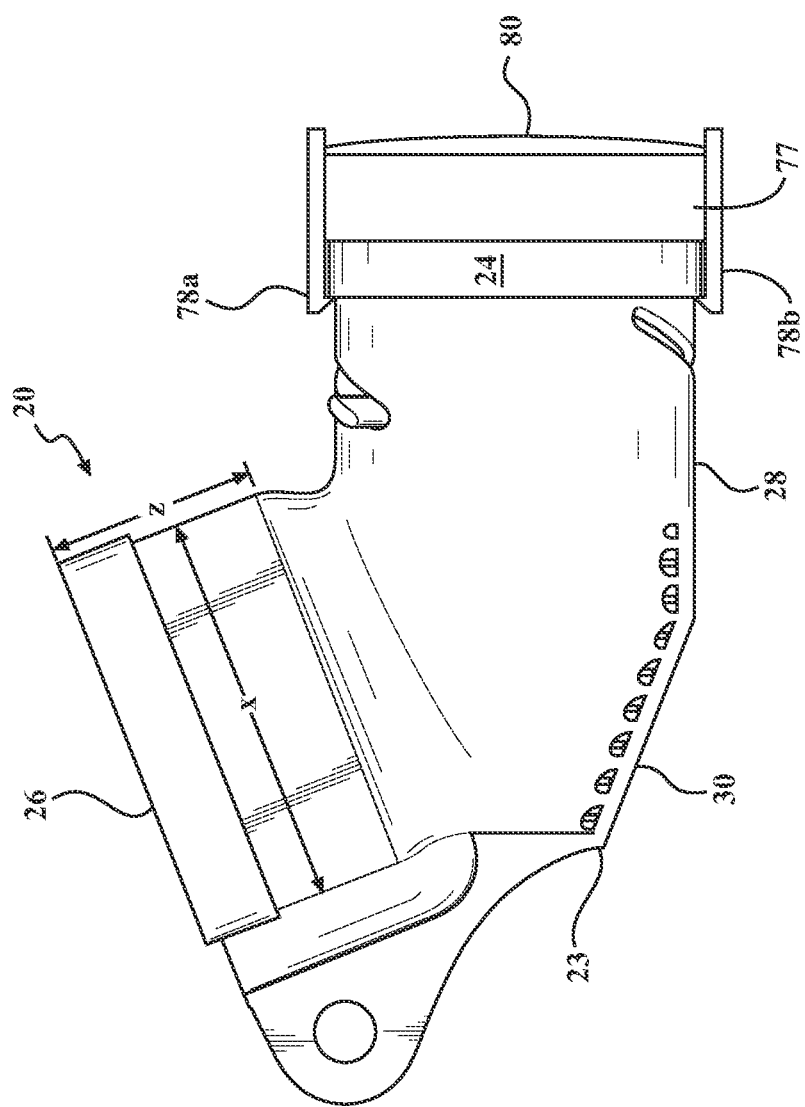

FIG. 10C
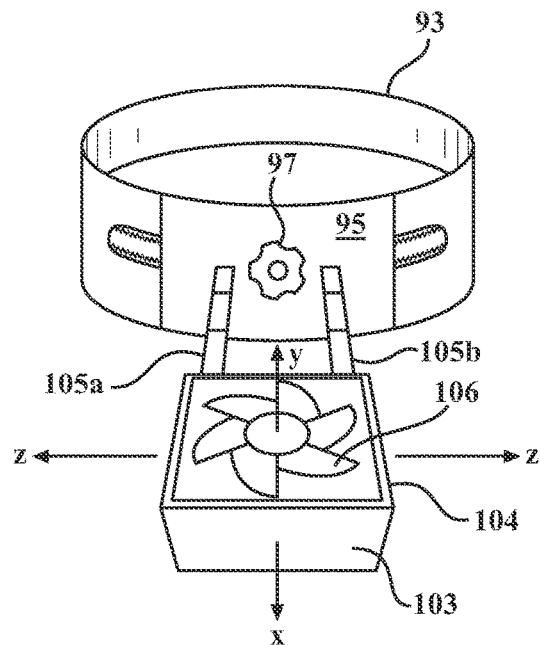
FIG. 11
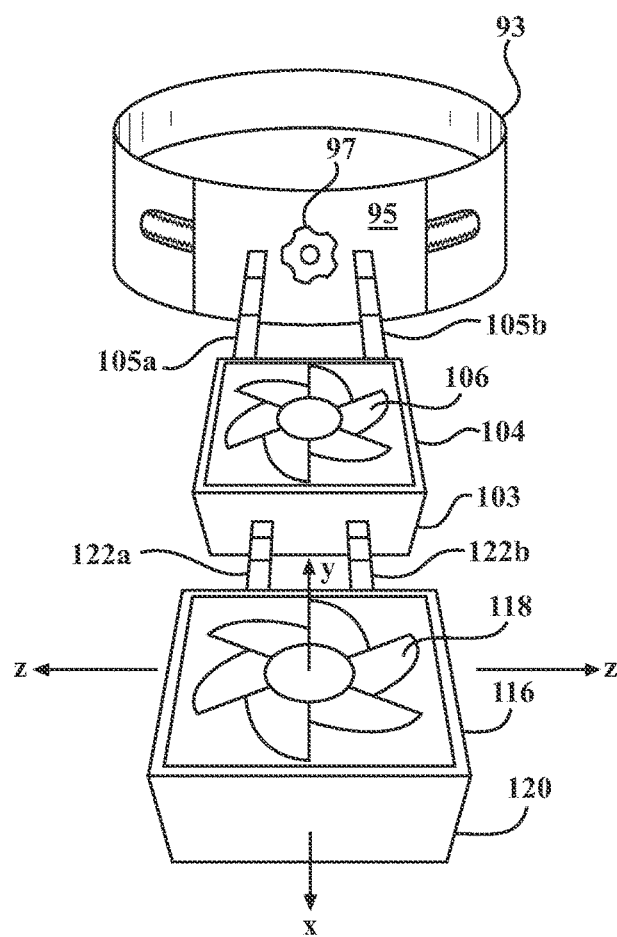
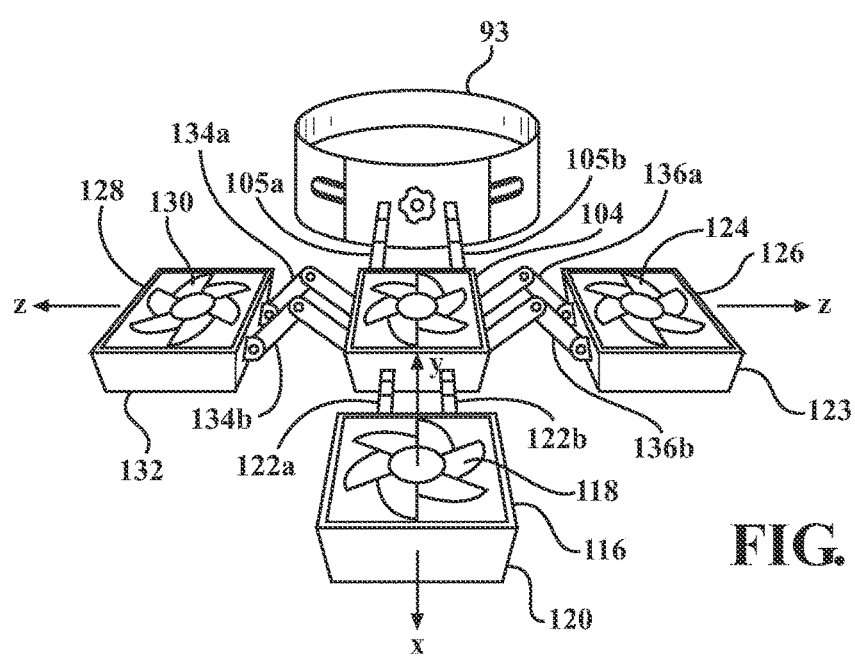
FIG. 12

FIG. 13A
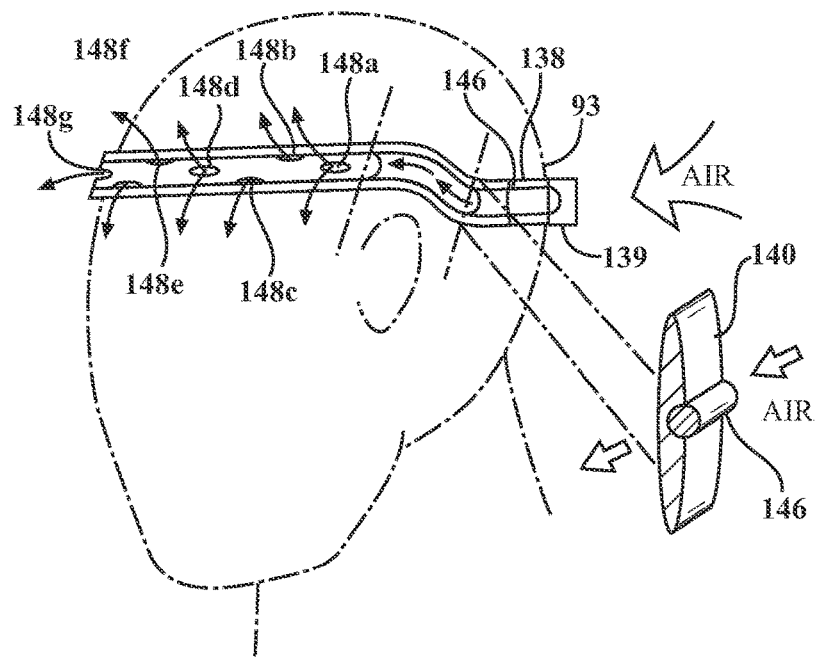
FIG. 13B
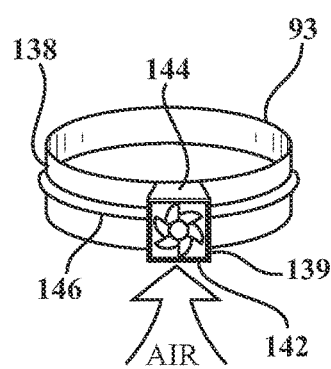
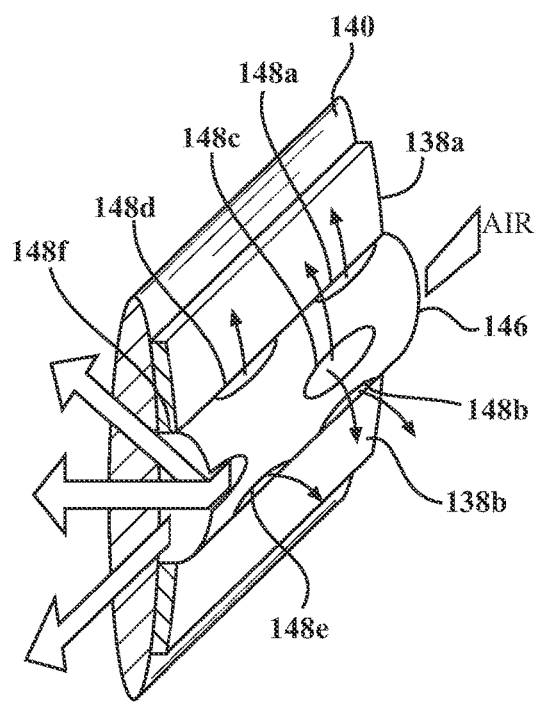
FIG. 13C
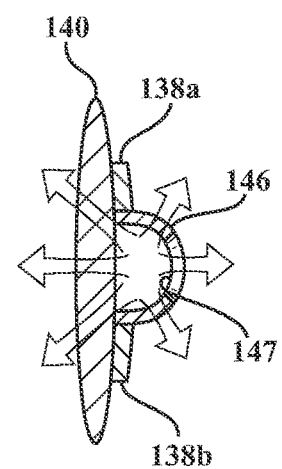
FIG. 13D

LIGHTING APPARATUS

CROSS-REFERENCE TO RELATED APPLICATIONS

This application is a continuation of U.S. patent application Ser. No. 15/502,078, filed on Feb. 6, 2017, which is a national phase entry of PCT/US15/43977, filed on Aug. 6, 2015, which claims the benefit of U.S. Provisional Patent Application No. 62/034,867, filed Aug. 8, 2014, the entirety of each of which is hereby incorporated by reference.

FIELD

This disclosure relates to lighting apparatuses, and in particular, surgical lighting apparatuses that can be worn on the head to illuminate a surgical site.

BACKGROUND

Certain known lighting apparatuses are worn on the head to provide focused illumination on an area of interest. One such lighting apparatus is a surgical headlamp, which is worn by a surgeon to illuminate a surgical site. In general, for a given spot width, spot adjustability, and brightness, it is desirable to minimize the weight and size of the headlamp.

Certain newer surgical headlamps use light emitting diodes (LEDs) as a source of illumination. Light emitting diodes are a cost-effective, efficient source of light. However, known LED-based surgical headlamps suffer from certain drawbacks. For example, in one design, the headlamp is affixed to a head band and positioned between the surgeon's eyes. This "between-eye" design provides a generally acceptable field of illumination, but limits the size of the headlamp to one that can fit between the surgeon's eyes without obstructing his or her vision. Such size limitations make it difficult to include features necessary to adequately dissipate heat from the LED or headlamp, which can cause heating to a temperature that is damaging to components or that is uncomfortably high for the surgeon to wear. The inability to dissipate heat sufficiently limits the brightness of the light emitted from the LED.

Other known designs place the headlamp above the surgeon's eyes. This design alleviates the space constraints of the "between-eye" design, allows for larger more efficient optics, and the ease of inclusion of heat sinks and/or fans that can dissipate heat. Thus the limitations on LED brightness that would otherwise exist are relaxed. However, as compared to the between-eye design, the "above-eye" design can produce inferior illumination caused by the light source no longer being in a near-centered position within the surgeon's line of sight. The resulting geometry can produce, for example, shadowing in recessed anatomy, or perceivable instrument shadows that were previously hidden from view behind the instruments. Additionally as the surgeon moves closer or further from the surgical site, the spot center will not track with the surgeon's narrow field of view as determined by their loops. In addition, many known designs require optical components such as mirrors in order to redirect the light emitted from the LED to the surgical site. Such optical components aid in relieving mechanical constraints but can be to the detriment of size, weight, optical efficiency and complexity of the headlamp.

In addition, it is often desirable to provide an optic that can be adjustably spaced from the LED. However, known designs require the use of external fasteners or engaging elements such as o-rings, springs, and screws to facilitate such adjustment. Such fasteners add to the complexity of the design, weight of the headlamp and diameter of the enclosure.

Thus, a need has arisen for a lighting apparatus that addresses the foregoing issues.

BRIEF DESCRIPTION OF THE DRAWINGS

FIG. 7A is a side elevation view of a modified example of the lighting apparatus of FIG. 1 with a secondary optic installed;

FIG. 7B is a front elevation view of the lighting apparatus of FIG. 7A;

FIG. 10C is a rear perspective view of an auxiliary fan system comprising a single fan module;

FIG. 11 is a rear perspective view of an auxiliary fan system comprising two fan modules;

FIG. 12 is a rear perspective view of an auxiliary fan apparatus comprising four fan modules;

FIG. 13A is a side elevational view of an auxiliary fan apparatus comprising a fan module integrated into a head band worn by a surgeon;

FIG. 13B is a rear perspective view of the auxiliary fan apparatus of FIG. 13A;

FIG. 13C is a close-up perspective view of a portion of a head band component of the auxiliary fan apparatus of FIGS. 13A and 13B;

FIG. 13D is a close-up side cross-sectional view of the head band component of FIG. 13C;

DETAILED DESCRIPTION

Figure 1:
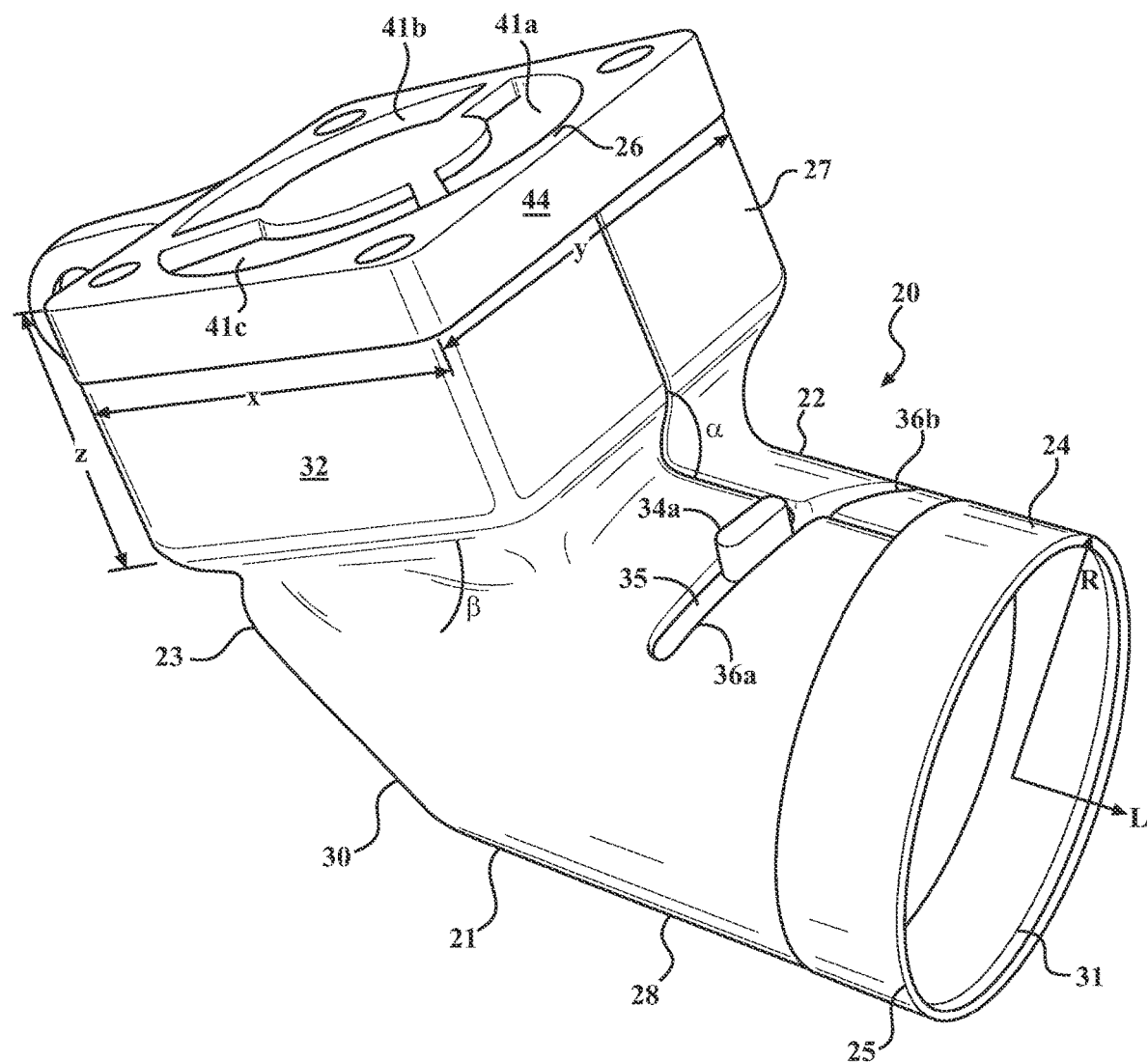
FIG. 1 is a perspective view of a first embodiment of a lighting apparatus in accordance with the present disclosure.

Described below are examples of lighting apparatuses and associated accessories such as undergown switches and auxiliary fans. In accordance with a first aspect of the present disclosure, a lighting apparatus is provided which comprises a housing having an outer surface and an inner surface. A light emitting diode is disposed in the housing, as can be an optical slide assembly comprising a slide and an optic disposed in the slide. The slide has an outer surface that frictionally engages the inner surface of the housing, the light emitting diode is spaced apart from the optic along an optical axis, and the slide assembly is slidable along the optical axis. In certain preferred examples, the housing and slide are engaged without the use of external fasteners such as springs, o-rings, washers, etc.

In accordance with a second aspect of the present disclosure, a heat sink is provided which comprises a frustoconical body having a length and a radial axis and a plurality of fins. The fins extend away from the body along the radial axis and are spaced apart from one another along the length axis. In certain examples, the heat sink is provided in a lighting apparatus housing and includes a recess in which a light emitting diode is disposed. In accordance with a third aspect of the present disclosure, a lighting apparatus is provided which comprises a housing, a heat sink disposed in the housing, and a light emitting diode. The heat sink has a proximal end and a distal end spaced apart by a length defining a length axis. The heat sink also has a recess extending a long a portion of the length. The light emitting diode has a mounting plane located in the recess of the heat sink between the proximal and distal end of the heat sink.

In accordance with a fourth aspect of the present disclosure, a lighting apparatus is provided which comprises a housing, a light emitting diode disposed in the housing and mounted on a printed circuit board, and an aluminum heat sink disposed in the housing. The light emitting diode has a thermal pad, and the heat sink has a pillar that is in thermal communication with the thermal pad via a thermal interface material.

In accordance with a fifth aspect of the present disclosure, a lighting apparatus is provided which comprises a housing, a light emitting diode disposed in the housing, a first optic comprising a lens in optical communication with the light emitting diode, and a second optic comprising a diffuser in optical communication with the lens and the light emitting diode. In certain examples, the diffuser is a holographic diffuser.

In accordance with a sixth aspect of the present disclosure, there is a lighting apparatus which comprises a light emitting diode having a thermal pad connected to a printed circuit board at a solder point. A temperature sensor is operatively connected to the solder point and generates a signal indicative of the solder point temperature. A controller is configured to generate a signal indicative of a drive current supplied to the light emitting diode and to receive the signal indicative of the solder point temperature. The controller is programmed to determine a nominal solder point temperature corresponding to the signal indicative of the drive current supplied to the light emitting diode and to adjust the speed of rotation of the fan based on the signal indicative of the solder point temperature and the determined nominal solder point temperature. In certain examples of the sixth aspect, a nominal solder point temperature database is created by determining a nominal operating junction temperature, providing a plurality of database light emitting diode drive current values that are less than a maximum drive current value, and calculating a database solder point temperature value corresponding to each database light emitting diode drive current temperature value and a determined nominal operating junction temperature value at which the level of noise of a fan is substantially equal to a desired level of noise.

In accordance with a seventh aspect of the present disclosure, a lighting apparatus is provided which comprises a light emitting diode and a switch operatively connected to the light emitting diode, wherein the switch is removably attachable to a surgical scrub and is operable to adjust the operation of the light emitting diode. In certain examples, the switch is operable through a surgical gown thus allowing switch functionality without compromising sterility of the surgeon or the surgical field.

In accordance with an eighth aspect of the present disclosure, a personal cooling apparatus is provided which comprises a head band and at least one fan module connected to the head band. In certain examples, the orientation of the fan module relative to the head band is adjustable. In accordance with other examples, the head band includes at least one internal passageway in fluid communication with at least one vent, and a fan module is connected to one end of the at least one internal passageway to direct air through the at least one internal passageway and out of the at least one vent. In accordance with further examples, a forced air, actively cooled lighting apparatus provides airflow for the personal cooling apparatus.

In accordance with a ninth aspect of the present disclosure, a lighting system is provided which comprises a lighting apparatus, a battery system, a vibrating motor, and a battery capacity detection controller. The lighting apparatus includes a housing and a light source disposed in the housing. The battery system comprises at least one fuel cell and a fuel cell capacity circuit, and the battery system is operatively connected to the light source. The battery capacity detection controller is operatively connected to the fuel cell capacity circuit, and the fuel cell capacity circuit is operatively connected to the battery capacity detection controller. The fuel cell capacity circuit is configured to transmit an output signal indicative of the fuel cell capacity to the battery capacity detection controller, the battery capacity detection controller is operatively connected to the vibrating motor, and the battery capacity detection controller is programmed to transmit a vibration signal to the vibrating motor based on the fuel cell capacity circuit output signal.

In accordance with a tenth aspect of the present disclosure, a method of illuminating a surgical field is provided. The method comprises providing a lighting system comprising a lighting apparatus and a battery system having at least one fuel cell, the lighting apparatus having a light source disposed in a housing. The method further comprises detecting a time remaining until the at least one fuel cell is at an end of life condition and vibrating a vibrating motor when the time remaining reaches a first value.

In accordance with an eleventh aspect of the present disclosure, a counterbalanced head band is provided which comprises a head band, a counterbalance mass, and a support connected to the head band. The counterbalance mass is connected to the support and spaced apart from the head band. In one implementation, a lighting apparatus is connected to the head band which comprises a housing and a light source disposed in the housing.

Referring to FIG. 1, a lighting apparatus 20 is depicted. Lighting apparatus 20 comprises a housing 22, a retention ring 24, and a fan 26. Housing 22 has a lower section 21 and an upper section 27. Lower section 21 includes a proximal end 23 and a distal end 25. Distal cylindrical section 28 defines a length axis L and a radial axis R. Lower housing section 21 also includes a proximal frustoconical section 30. The proximal frustoconical section 30 is oriented coaxially with the distal cylindrical section 28 but has a radius that narrows when moving in the proximal direction (i.e., in a direction away from distal end 25) along the length axis L. The proximal end 23 and distal end 25 of the lower housing section 21 are spaced apart along the length axis L.

Housing 22 also includes an upper section 27 that comprises a fan section 32 in which fan 26 is located. The fan section 32 has a first axis x that is oriented orthogonally to a second axis y and a third axis z. A plane defined by the y and z axes intersects the length axis L of the lower housing section 21 at a non-orthogonal angle α that is preferably obtuse. A plane defined by the x and y axes intersects the length axis at an angle β which is preferably acute. Fan 26 includes blades 52 (not shown) which rotate in a plane parallel to the x-y plane to create an exhaust air flow along the z-axis.

Figure 3:
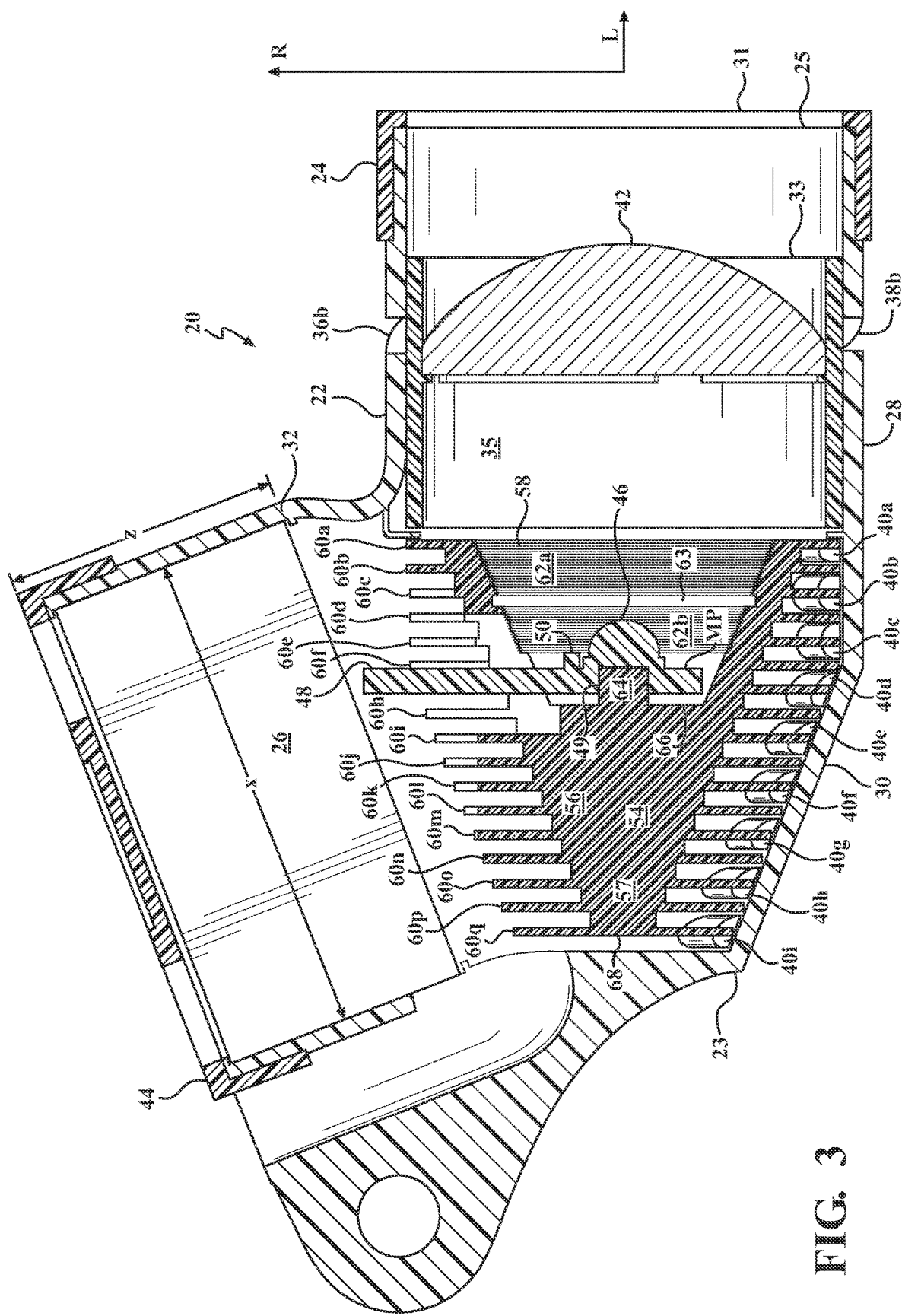
FIG. 3 is a side cross-sectional view of the lighting apparatus of FIG. 1.

Referring to FIG. 3, lighting apparatus 20 includes a light source. In the illustrated example, the light source is a light emitting diode 46, which may comprise a single die or an array of dies. Lighting apparatus 20 also includes an optic assembly 33. Optic assembly 33 comprises an optical slide 35 and an optic 42. Optic 42 may comprise, for example, a lens, a diaphragm, a diffuser, a filter or a combination thereof. Preferred lenses include plano convex, biconvex, and total internal reflection (TIR) lenses. When lighting apparatus 20 is used for surgical applications, in certain examples, the optic 42 has a diameter that is preferably no greater than about 40 mm, more preferably no greater than about 35 mm, and still more preferably no greater than about 30 mm. At the same time, the optic diameter is preferably at least about 10 mm, more preferably at least about 15 mm, and still more preferably at least about 20 mm. In certain examples, optic 42 comprises a lens with an incident (light receiving) surface facing light emitting diode 46 and a transmissive (light transmitting) surface, facing away from light emitting diode 46 and a normal vector projected from the incident surface of the optic 42 intersects the light emitting diode 46. In the same or other examples, light emitting diode 46 emits light along a light transmission path, at least a portion of which is along the length axis L, and the light transmission path intersects optic 42.

Light from the light source 46 travels to the optic 42 in a direction that defines an optical axis which is parallel to the length axis L of the distal cylindrical section 28 of housing lower section 21. Retention ring 24 defines a light transmission opening 31 through which light is transmitted from the lighting apparatus 20 to an area of interest. When the lighting apparatus 20 is used for surgical applications, the area of interest is generally a surgical field defined by an area on or in the body of a patient undergoing a surgical procedure.

Figure 2:
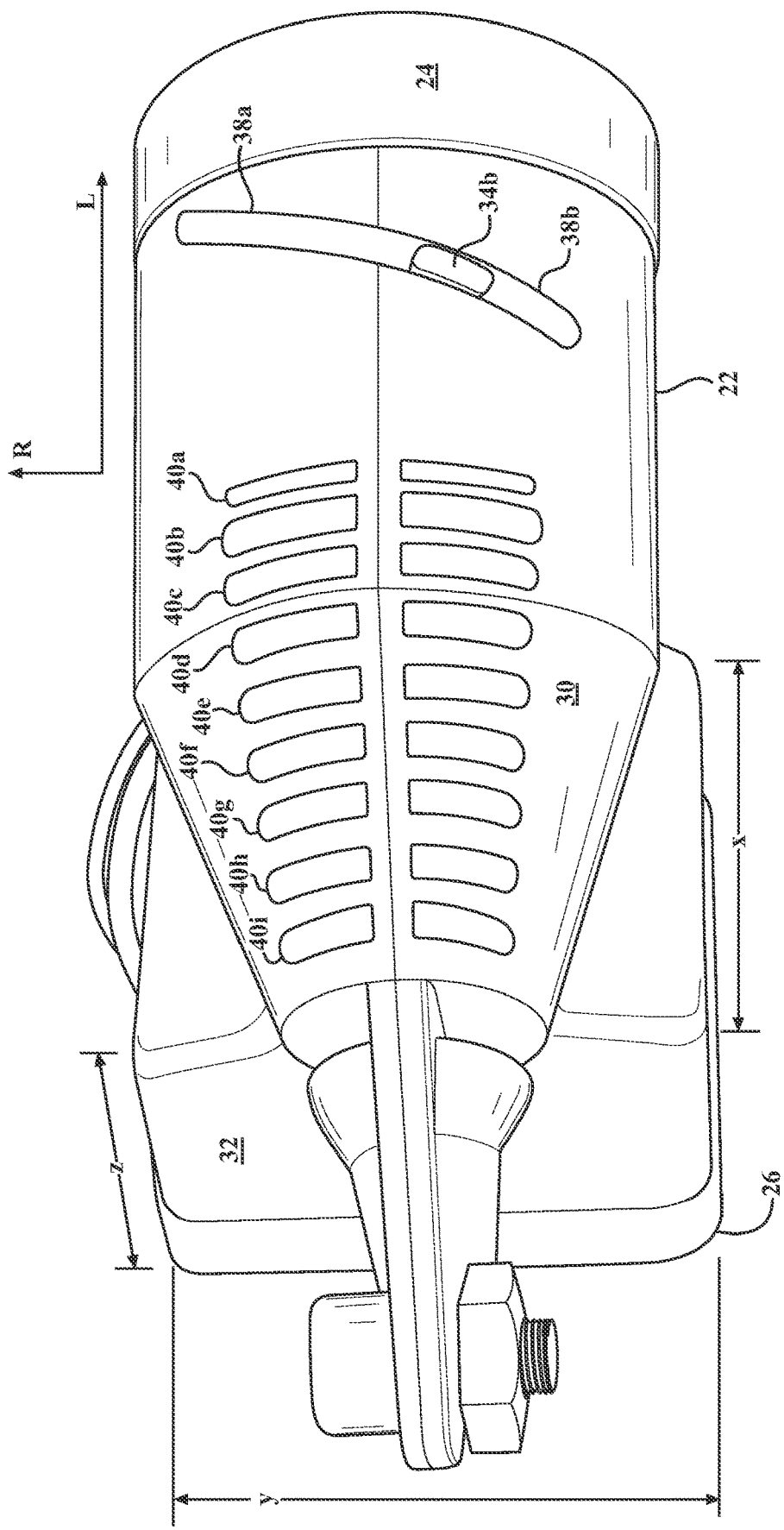
FIG. 2 is a bottom plan view of the lighting apparatus of FIG. 1.
Figure 4:
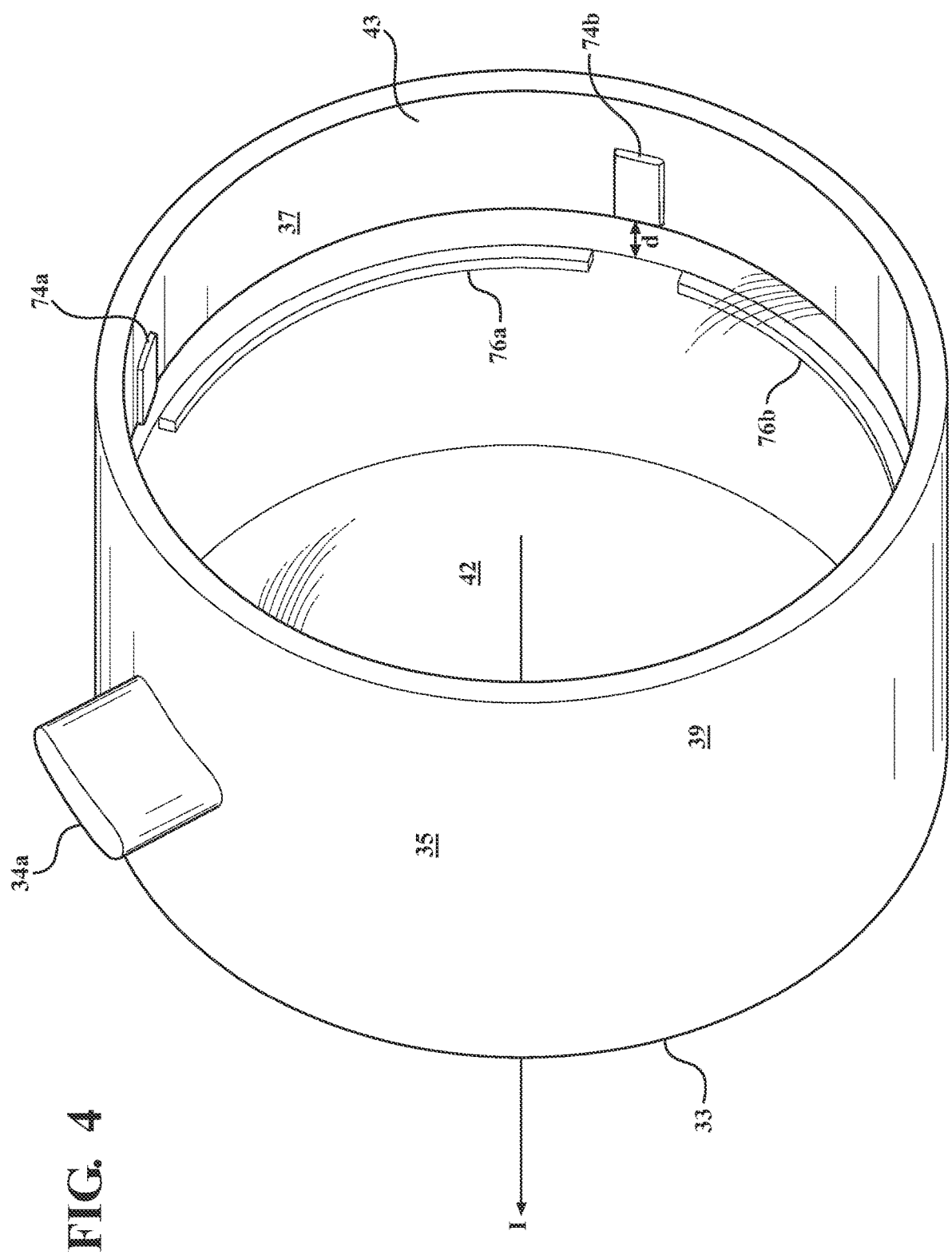
FIG. 4 is a perspective view of an optical assembly comprising a slide with an installed lens used in the lighting apparatus of FIG. 1.

In the example of FIGS. 1-3, optic assembly 33 is movable along the length axis L toward and away from light source 46. An exemplary optical assembly 33 is shown in FIG. 4. In the depicted example, optical slide 35 includes a radially inner surface 37 and a radially outer surface 39. Radially outer surface 39 frictionally engages the inner wall of the distal cylindrical section 28 of housing lower section 21 so that the optical slide 35 may be repositioned to desired locations along the length L axis relative to the light source 46. In preferred examples, and as illustrated in FIGS. 1-3, the optical assembly 33 engages the housing 22 without the use of springs, fasteners, or other mechanical devices other than housing 22 and the optical slide 35 themselves.

Optical slide 35 includes two bosses 34a (FIGS. 1 and 4) and 34b (FIG. 2) which are spaced apart along the radial axis R from one another. Although only two are depicted, additional bosses may be provided. Bosses 34a and 34b are manipulable by a user to adjust the position of optical slide 35 along the length axis L. In the example of FIGS. 1-3, boss 34a engages a groove comprising two groove halves 36a and 36b (FIG. 1). The groove halves 36a and 36b are formed in the distal cylindrical section 28 of housing lower section 21 and extend from the inner surface of the distal cylindrical section 28 to the outer surface of the distal cylindrical section 28. Groove halves 36a and 36b jointly define a single groove that extends along a portion of the length of distal cylindrical section 28 and around a portion of the circumference of distal cylindrical section 28. The single groove defined by groove halves 36a and 36b restrains the movement of the boss 34a along the length axis L and limits the range of movement of the optical slide 35 along the length axis. In preferred examples, the optical assembly 33 does not include external fasteners for retaining optic 42 to optical slide 35, such as retention rings, threaded collars, screws, adhesives, cements, or other fastener hardware.

In the example of FIGS. 1-3, the housing 22 is formed as two mateable halves. The first mateable half includes half groove 36a, and the second mateable half includes half groove 36b. The mateable halves are held together by retention ring 24 which slides over a portion of the distal end of distal cylindrical section 28 of housing lower section 21. Fan grill cap 44 may also be provided to hold together the two mateable halves of housing 22. The mateable halves may be held together by additional means, such as adhesives, fasteners, etc. Thus, as boss 34a is moved from half groove 36a to half groove 36b, the optical slide 35 moves along the length axis L in a direction away from the light source 46. As shown in FIG. 2, distal cylindrical section 28 of housing lower section 21 also includes half grooves 38a and 38b which mate to form a single groove. Boss 34b projects through the single groove defined by groove halves 38a and 38b and in a preferred embodiment does not extend radially past the external wall of section 28 to avoid entering the user's line of sight. As boss 34a is manipulated, boss 34b is connectedly moved from half groove 38b to half groove 38a, and the optical slide 35 moves along the length axis L in a direction away from the light source 46. Thus, a user can manipulate one or both of bosses 34a and 34b within their respective grooves to adjust the length axis position of optical slide 35 and optic 42. The inclusion of two or more opposite grooves such as the first groove defined by half grooves 36a and 36b and the second groove defined by half grooves 38a and 38b balances the length L axis force exerted by the inner surface of the housing distal cylindrical section 28 against the optical slide radially outer surface 39 around the circumference of the outer surface 39

Referring to FIG. 4, optical slide 35 includes ring stops 76a-76d (only 76a and 76b are visible) and bumpers 74a-74d (only 74a and 74b are visible). Ring stops 76a-76d form ledges that are spaced apart from one another around the inner circumference of the optical slide 35. Each ring stop 76a-76d projects inwardly along the radial axis R. A distal face of each ring stop 76a-76d abuttingly engages a portion of a proximal face of optic 42. Each bumper 74a-74d projects slightly inwardly along the radial axis R, albeit by a shorter distance than the rings stops 76a-76d. The bumpers 74a-74d are spaced apart from the ring stops 76a-76d by a distance d along the insertion axis I (which is the length axis of the optical slide 35). In certain examples, the bumpers 74a-74d have a thickness that tapers as you move away from the ring stops 76a-76d to facilitate sliding engagement of the optic 42 and the bumpers 74a-74d, along the insertion axis I. In FIG. 4, circumferentially spaced gaps are shown between the ring stops 76a-76d so that the ring stops 76a-76d can be injection molded. However, in other examples, the ring stops 76a-76d may comprise a single, continuous ring stop.

Together, each ring stop 76a-76d cooperates with two of the bumpers 74a-74d to define a "seat" which is an area in which the optic 42 is retained. The seat comprises an axial distance d between the proximal end of the bumpers 74a-74d and the distally facing surface of the ring stops 76a-76d.

The optical slide 35 is preferably resilient and designed to allow the optic 42 to snap-fittingly engage the slide 35 in the seat. In one method, a user inserts the optic in the open distal end 43 (FIG. 4) of optical slide 35 in the insertion direction I shown in FIG. 4 (i.e., along the length axis of the slide 35). During insertion, the proximal (light receiving) face of the optic 42 initially engages the bumpers 74a-74d, and because of the diameter of the optic 42 and the thickness of the bumpers 74a-74d, the optic 42 forces the bumpers 74a-74d to flex outwardly along the radial axis R. As the insertion of the optic 42 continues, the proximal (light receiving) face of the optic 42 eventually engages the distal face of the ring stops 76a-76d and the distal (light transmitting) face of the optic 42 slides over the bumpers 74a-74d. When the optic 42 passes the bumpers 74a-74d, the outwardly deforming force exerted by optic 42 against the bumpers 74a-74d is removed, and the optical slide 35 returns to its relaxed (undeformed) state. At this point, the optic 42 is securely located in the seat defined between the bumpers 74a-74d and the ring stops 76a-76d such that the proximal (light receiving) face of the optic 42 engages the ring stops 76a-76d and the distal (light transmitting) face of the optic 42 engages the bumpers 74a-74d. In certain examples, optical slide 35 is integrally formed to include bumpers 74a-74d and ring stops 76a-76d. In certain implementations, optical slide 35 is integrally molded with bumpers 74a-74d and ring stops 76a-76d from a plastic that is semi-rigid but somewhat elastically deformable after molding.

As mentioned previously, light source 46 may comprise a single light emitting diode or an array of diodes. In certain examples, light source 46 comprises a light emitting diode comprising one or more dies having a total power output that is at least about 5 W, preferably at least about 7 W, and more preferably at least about 9 W. At the same time, the one or more dies in such examples have a power output that is no more than about 20 W, preferably no more than about 15 W, and still more preferably no more than about 12 W. Suitable single die light emitting diodes include the XM-L2 light emitting diodes supplied by Cree, Inc. of Durham, N.C. Suitable multi-die diodes include the Cree MK-R diodes and the XM-L Color, the latter having a plurality of color dies making it suitable for discreet color selection or color mixing. The XM-L2 diode is a single die light emitting diode with a maximum suggested drive current of about 3 amps and a maximum suggested power of about 10 Watts although it is possible to safely operate the LED at higher Wattage. The maximum light output at 10 Watts and 85° C. is 1052 lumens. The MK-R is a multi-die array light emitting diode with a maximum drive current of 2.5 amps, a maximum power of 15 W, and light output of 1769 lumens at 15 W and 85° C.

In certain examples, lighting apparatus 20 is designed for use as a surgical lamp. In accordance with certain surgical lamp applications, the optical slide 35 is movable from a first position to a second position along the length axis of the distal cylindrical section 28 such that light emitted from the housing 22 at a distance of about 18 inches from the light emitting diode 46 has a first diameter when the optical slide 35 is in the first position along the length axis L and a second diameter when the optical slide 35 is in the second position along the length axis L, and the second diameter is at least three times, preferably at least five times, and more preferably at least about twelve times the first diameter. With respect to the "first" and "second" positions of the optical slide 35 described above, the first optical slide 35 position is farther from the light emitting diode 46 along the length L axis than is the second optical slide 35 position. In addition, the foregoing relative relationships between the spot diameters in the first and second positions are based on a 90 degree angle of incidence of the light on a surface on which the diameter is measured.

In the same or other examples, when the optical slide 35 is in the first position along the length axis, the spot diameter at a distance of about 18 inches from the light emitting diode 46 is no more than about 1.5 inches, more preferably no more than about 1.0 inches, and still more preferably no more than about 0.5 inches, and when the optical slide is in the second position along the length axis, the spot diameter at a distance of about 18 inches from the light emitting diode 46 is at least about 4.5 inches, preferably at least about 6 inches, and still more preferably at least about 7 inches. The foregoing diameters are based on a 90 degree angle of incidence of the light on a surface on which the diameter is measured.

Lighting apparatus 20 is preferably designed to transfer heat generated by light source 46 to the surrounding environment. To facilitate such heat transfer, a heat sink 54 is provided in the interior of proximal frustoconical section 30 of lower housing section 21, as shown in FIG. 3. In certain examples, heat sink 54 is preferably formed from a thermally conductive material having a thermal conductivity (at 25° C.) of at least about 150 W/(m° C.), preferably at least about 175 W/(m° C.) and still more preferably at least about 200 W/(m° C.). Aluminum, copper, thermoplastic or carbon materials such as graphite are preferred heat sink 54 materials. However, aluminum is especially preferred because of its relatively lower weight and cost, and relatively high thermal conductivity. In certain examples, heat sink 54 consists essentially of aluminum. In other examples, heat sink 54 consists essentially of aluminum but has one or more surfaces that are copper plated, inset, or inlaid to facilitate thermal solder connection to the thermal pad of a light emitting diode used as light source 46. In another embodiment, high thermal conductivity materials, such as copper pillars or copper heat pipes can be inset or integrated into the comparatively lower thermal conductivity heat sink 54, made of material such as aluminum, to enhance conduction of heat away from the light emitting diode thermal pad, while enabling the use of solder as a high efficiency thermal interface material. Copper pillars, insets or heat pipes can span across all or a portion of the heat sink 54. They can be thermally connected to the heat sink by a thermal interface material such as solder, Arctic Silver, or a comparable efficiency thermal grease or adhesive. In another embodiment portions of the pillar can be electrically isolated from one another to allow direct heat sink 54 soldering to the light emitting diode 46 anode and cathode pads as well as the thermal pad without creating a short within the circuit. Electrical isolation of heat sink 54 portions can facilitate the use of each portion as both heat sink and conductor to the light emitting diode anode or cathode pads. In contrast to the relatively thermally conductive heat sink 54, the housing 22 is preferably relatively thermally insulating to provide a greater degree of comfort to the user of the lighting apparatus 20 notwithstanding the heat generated by light emitting diode 46. Heat sink 54 is proximally adjacent to optical assembly 33, and the optical assembly 33 is movable along the length axis L relative to the heat sink 54. Optic 42 includes a proximal (light receiving) face that is located between the optic's distal (light transmitting) face and the heat sink 54. Thus, manipulation of bosses 34*a* and 34*b* adjusts the spacing between the optic assembly 33 and the heat sink 54 along the length axis L.

Figure 5:
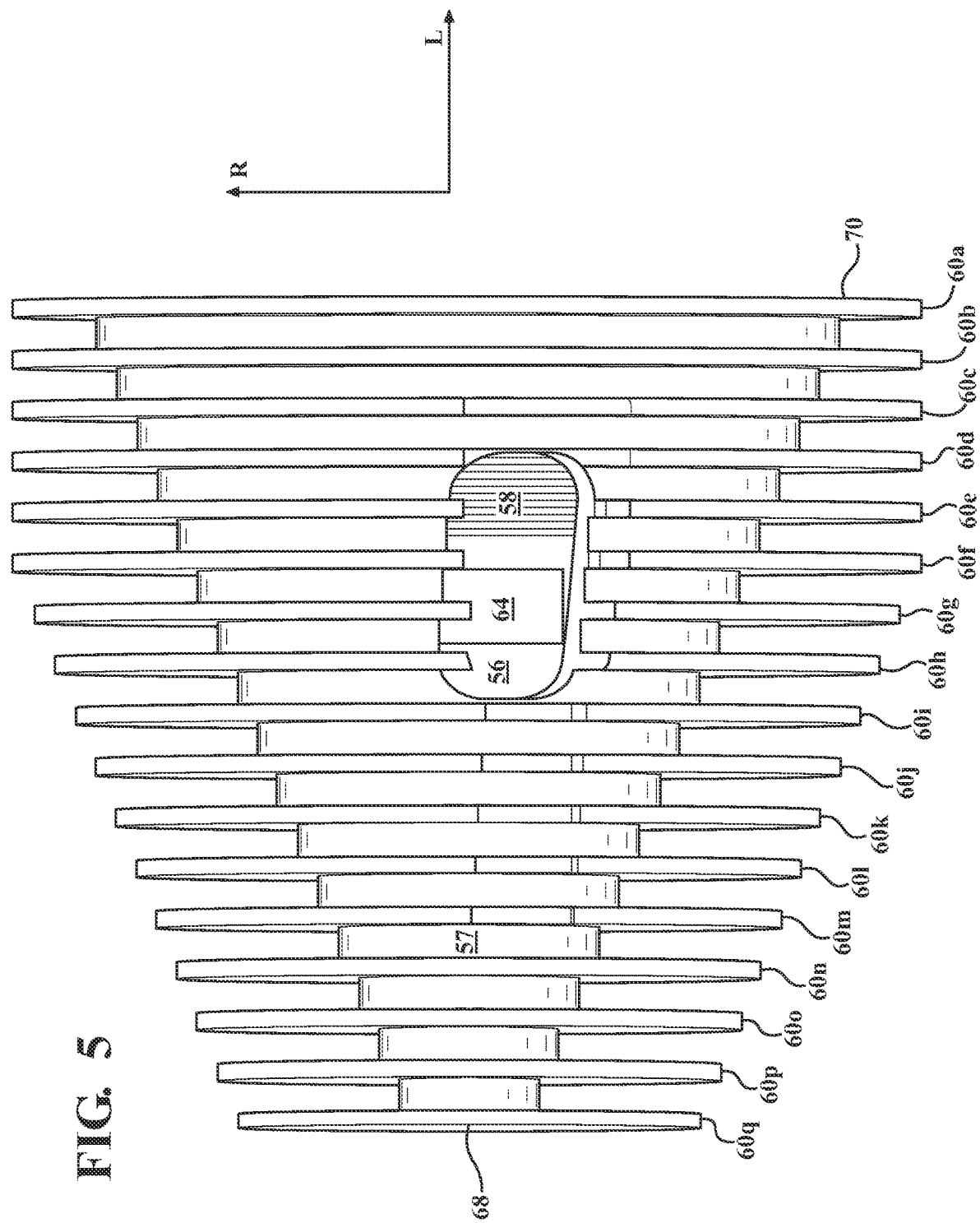
FIG. 5 is a side elevational view of a heat sink used in the lighting apparatus of FIG. 1.
Figure 6:
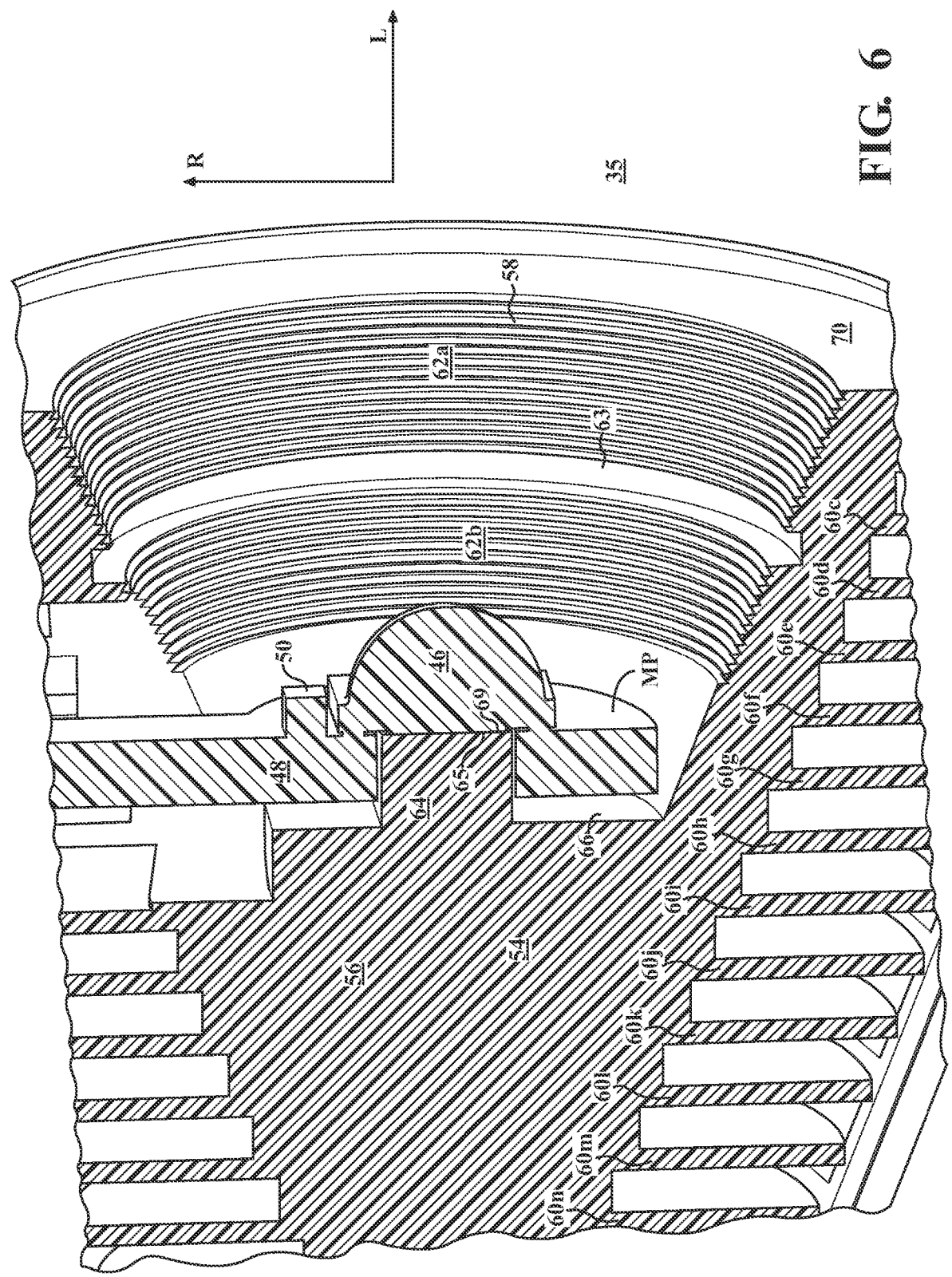
FIG. 6 is a close-up, side-cross sectional view of the heat sink, light emitting diode, and printed circuit board of the lighting apparatus of FIG. 1.

Heat sink 54 may be a variety of shapes, including conical, cylindrical, and frustoconical. In certain examples, a recessed heat sink shape is preferred, and a recessed frustoconical heat sink shape is more preferred. In the example of FIGS. 3, 5, and 6, heat sink 54 comprises a frustoconical body 56 having a length axis and a radial axis parallel to the length axis L and radial axis R of the distal cylindrical section 28 of lower housing section 21 (FIG. 3). Heat sink 54 further comprises a plurality of fins 60*a*-60*q* that extend around all or part of the circumference of heat sink 54 and project away from the heat sink body 56 along the radial axis R. Fins 60*a*-60*q* are annular in shape and increase the surface area for heat transfer from heat sink 54 to ambient air flowing through housing 22. Fins 60*a*-60*q* are spaced apart from their adjacent neighbors along the length axis L. Each adjacent pair of fins in the set of fins 60*a*-60*q* defines a circumferential channel around heat sink body 56 for air to flow through en route from housing intake vents 40*a*-40*i* to the intake of fan 26 (FIG. 3).

In certain examples, and as shown in FIGS. 3 and 6, heat sink 54 includes a solid portion 57 and a recessed portion 58. The recessed portion 58 is distally adjacent the solid portion 57 along the length axis L. Solid portion 57 includes the proximal end 68 of the heat sink 54, and recessed portion 58 includes the distal end 70 of the heat sink 54. The diameter of the solid portion 57 along the radial axis R increases when moving from the proximal end 68 of the heat sink 54 toward the distal end 70 of the heat sink 54. The recessed portion 58 has a recess diameter along the radial axis R which increases when moving in a direction toward the distal end 70 of the heat sink 54 and away from the proximal end 68 of the heat sink. The inner surface of the recessed portion 58 of heat sink 54 may include light controlling features, examples of which include light absorbing, diffusing, or reflective coatings. Alternatively or additionally, the inner surface of the recessed portion 58 of heat sink 54 may include textured surface features that are light controlling, such as grooves, steps, ridges, or fins. In the example of FIG. 6, the inner surface of the recessed portion 58 includes first and second sets of circumferential ridges 62*a* and 62*b* which are spaced apart from one another along the length axis L by circumferential groove 63. The ridges each have a proximal and a distal face, and the proximal faces slope in a direction toward solid portion 57 and away from the distal end 70 of heat sink 54 to reflect light back toward light emitting diode 46 and provide a diffusing effect. In addition, the inner surface of the recessed portion 58 includes a black anodized coating for absorbing light from the light emitting diode 46. In certain examples, a coating provided on the inner surface of recessed portion 58 absorbs from about 60 percent to about 90 percent, preferably from about 65 percent to about 85 percent, and more preferably from about 70 percent to about 80 percent of light incident on the inner surface of recessed portion 58.

Referring to FIGS. 3 and 5, heat sink 54 has a closed proximal end 68, and an open distal end 70. The body 56 has an outer diameter that increases when moving from the proximal end 68 to the distal end 70, and which preferably increases monotonically when moving from proximal end 68 to distal end 70. Fins 60*a*-60*q* each have an outer diameter. The outer diameters of a first subset 60*q* to 60*f* of fins 60*a*-60*q* progressively increase when moving away from proximal end 68 along the length axis L. In certain examples, and a shown in FIG. 3, the outer diameters of the first subset 60*q*-60*f* of fins 60*a*-60*q* increase linearly when moving from proximal end 68 toward distal end 70 of heat sink 54.

A second subset 60*f*-60*a* of fins 60*a*-60*q* have has substantially equal outer diameters. The first subset 60*q*-60*f* is proximally adjacent the second subset 60*f*-60*a* along the length axis L.

In the example of FIG. 3, light emitting diode 46 has a mounting plane (MP), which is the proximal-most plane of the pads of light emitting diode 46. The mounting plane MP is located in the recessed portion 58 and spaced apart from the heat sink distal end opening 70 in the proximal direction along the length axis L. In certain examples, and as also illustrated in FIG. 3, the entire light emitting diode 46 is located within recessed portion 58 and spaced apart from the heat sink distal end opening 70 in the proximal direction along the length axis L.

Heat sink 54 acts as a thermal conduit that provides a path for a heat flux in the distal to proximal direction along the length axis L and radial axis R. As shown in FIG. 3, fins 60*a*-60*f* are spaced apart from the light emitting diode 46 and its mounting plane (MP) in the distal direction along the length axis L. In addition, housing air intake vents 40*a*-40*c* are spaced apart from light emitting diode 46 and its mounting plane in the distal direction. Thus, heat sink 54 is configured to receive heat distally of the light emitting diode 46 and provide a path for thermal conduction from the distal end 70 of the heat sink 54 to the proximal end 68 of the heat sink 54. In many known lighting apparatus designs, there is no convectively useful heat sink portion provided distally of the light source mounting plane which does not also serve as a portion of the exterior housing. Accordingly in other said designs, any heat generated by the light source that is conducted to the housing for convective cooling simultaneously limits the wattage of the light source to a level that can be adequately cooled without becoming uncomfortably hot for the user. In contrast, heat sink 54 and housing 22 are configured so that convective heat transfer occurs distally of the light emitting diode 46 via air flowing in the intake vents 40a-40c and contacting fins 60a-60f Heat sink 54 can reach temperatures high enough to adequately convectively cool a high wattage light source with relaxed concern for external housing temperature because heat sink 54 is both independent from and insulated by the housing 22. Note that while fins 60a-60q are depicted as parallel to the radial axis R, they may also tilt in the proximal or distal directions.

Without wishing to be bound by any theory, the recessed, heat sink 54 depicted in FIGS. 3, 5, and 6 is believed to yield unexpected benefits in dissipating heat generated by light emitting diode 46. First, providing a recessed heat sink allows diode 46 to be placed in the recess such that heat sink material is provided distally of the diode mounting plane MP. As a result, the heat sink can be shortened (along the proximal to distal direction) while still transferring heat at rates comparable to longer, non-recessed heat sinks.

Second, light emitting diode 46 projects light in a generally frustoconical pattern. By providing a frustoconical recess 58, the heat sink inner surface profile more closely tracks the emitted light pattern thus minimizing interference with light transmission to the lens as well as minimizing the internal, and accordingly the external, heat sink diameters. While conical heat sinks may provide such advantages, the restriction in heat transferring material proximate their tips may provide a dead zone of relatively little heat transfer.

Fan 26 provides a means for increasing convective heat transfer to the ambient air surrounding the lighting apparatus 20. In certain implementations, when fan 26 is activated, ambient air is drawn in through housing intake vents 40a-40i and flows between adjacent pairs of fins in the set of fins 60a-60q. The air picks up heat from the heat sink 54 as it contacts the fins 60a-60q and the body 56 and is pulled to the intake of fan 26. The heated air is then exhausted from fan exhaust vents 41a-41c (FIG. 1) to the atmosphere.

Referring again to FIG. 3, in certain examples, solid portion 57 of heat sink 54 includes a distal face 66 spaced apart from the proximal end 68 of heat sink in the distal direction along the length axis L. A pillar 64 projects distally away from a central portion of distal face 66 and serves as an interface to the light emitting diode 46. Light emitting diode 46 is mounted on a printed circuit board 48. Printed circuit board 48 includes an opening 49 through which pillar 64 projects. A thermal interface material 69 (FIG. 6) is applied and bonded to distal face 65 of pillar 64 and to the thermal pad (not separately shown) of light emitting diode 46. In certain examples, the thermal interface material 69 is a thermally conductive adhesive. In other examples, the thermal interface material 69 is a solder.

Suitable thermally conductive adhesives include those comprising silver. Examples of such suitable thermally conductive adhesives include Arctic Silver™ Silver Adhesive supplied by Arctic Silver, Inc. of Visalia, Calif. Preferred thermally conductive adhesives have a thermal conductivity of at least about 1.0 W/(m° C.), preferably at least about 1.5 W/(m° C.), more preferably at least about 3 W/(m° C.), still more preferably at least about 6 W/(m° C.), and even more preferably at least about 8 W/(m° C.). The foregoing configuration provides a thermally conductive path from the thermal pad of light emitting diode 46 to heat sink 54, wherein the printed circuit board 48 does not lie within the thermally conductive path. The configuration beneficially improves heat transfer because the printed circuit board tends to be thermally insulating in nature, and reduces the degree of heat transfer from the thermal pad of light emitting diode 46 to the heat sink 54.

In general, aluminum is a preferred material of construction for heat sink 54 relative to copper because aluminum's density is approximately ⅓ that of copper. In general, aluminum bonds poorly to solder, making solder a poor thermal interface material. However, in certain examples, heat sink 54 is constructed from aluminum but includes a thin copper plating or anodizing on the distal face 65 of pillar 64. The copper plating allows solder to be used effectively as a thermal interface material 69 which is preferable due to its high thermal conductivity because it is often many times greater that of other thermal interface materials. The same plating or anodizing technique can be used to allow soldering of the copper pillar or heat pipe to the aluminum heat sink. Thus, in this example, heat sink 54 benefits from the relatively lower density of aluminum while at the same time enabling for the use of solder as a high efficiency thermal interface material.

In some examples, light emitting diode 46 is in direct optical communication with optic 42 as there are no intervening optical components between light emitting diode 46 and optic 42. However, in accordance with the fourth aspect, lighting apparatus 20 may be provided with multiple optics. In one example, optic 42 comprises a lens of the type described previously, and an optical diffuser (not shown) may be fixed in the groove 63 within the recessed portion 58 of heat sink 54. The optical diffuser may be a holographic diffuser and may be provided as a sheet or plate, or can be integrated with other optics as a coating or film. The holographic diffuser scatters light received from light emitting diode 46 at precise angles of distribution such as 0.5, 1, 3, 5, and 10 degrees, for example. In certain implementations, some length axis positions of optical assembly 33 may yield a focal point that causes artifacts, such as hot spots or an image of the die structure of the light emitting diode 46, to be projected from lighting apparatus 20, which is undesirable. The scattering effect of the holographic diffuser homogenizes the light minimizing and preferably eliminating such artifacts.

Preferred optical diffusers have a defined scatter angle, and preferred scatter angles are from about 0.5 degrees to about 10 degrees, more preferably from about 3 degrees to about 8 degrees, and more preferably from about 4 degrees to about 6 degrees. Suitable optical diffusers include film sheet, holographic diffusers supplied under the name LSD® by Luminit, LLC of Torrance, Calif. In other examples, the optical diffuser may be provided as a coating on a lens used as optic 42. In preferred examples, lighting apparatus 20 does not include an iris or a mirror.

In certain examples, the lighting apparatus 20 may include another optic in addition to or in lieu of the optical diffuser provided in groove 63. Referring to FIG. 7, a secondary optic assembly comprising a secondary optic housing 77 and a secondary optic 80 may be provided. The secondary optic assembly is located distally of the optic 42. Secondary optic housing 77 can include fastening features such as latch portions 78a and 78b which resiliently flex outward radially to engage a lip defined by retention ring 24. Secondary optic 80 may be positioned at or slightly distally of opening 31 in distal cylindrical section 28 of lower housing section 21. The secondary optic may comprise any of the types of optics described previously for optic 42.

In certain examples, fan 26 provides a means for controlling the junction temperature ($T_j$) of the light emitting diode 46. Light emitting diodes include a P-N junction. Electrical energy that is not converted to light is converted to heat at the P-N junction. As is known to those skilled in the art, it is generally desirable to maintain a low junction temperature to prolong the life of light emitting diode 46. Conversely, it is undesirable to consume energy to operate fan 26 or to maximize its speed if the junction temperature is acceptable. Thus, in certain examples, lighting apparatus 20 is operably connected to a controller that is programmed to control the junction temperature of light emitting diode 46.

Although the diode junction is a critical location of temperature control, it is generally not possible to measure the junction temperature. However, as known to those skilled in the art, the junction temperature $T_j$ is related to the solder point temperature $T_{sp}$. The solder point of light emitting diode 46 is the location where the light emitting diode 46 is soldered to a printed circuit board. The junction temperature can be determined from the solder point temperature using the following relationship:

$$T_j = T_{sp} + \theta_{th} P_{total} \quad (1)$$

where, $T_j$=junction temperature (° C.);
$T_{sp}$=solder point temperature (° C.)
$\theta_{th}$=Thermal resistance of light emitting diode (° C./W)
$P_{total}$=Total input power to the light emitting diode (W)

The total input power to the light emitting diode can be determined as follows:

$$P_{total} = I_f V_f \quad (2)$$

where, $I_f$ is the forward (drive) current (amps)
$V_f$ is the forward voltage (volts)

Figure 15:
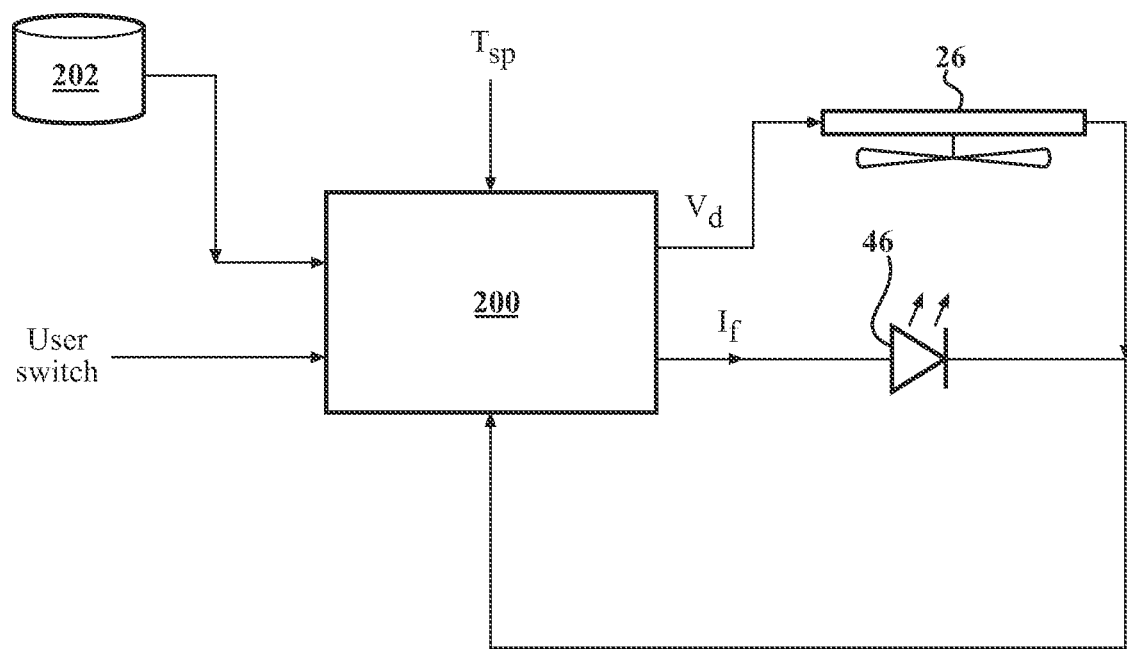
FIG. 15 is a schematic of a control system for controlling the junction temperature or solder point temperature of a light emitting diode in a lighting apparatus in accordance with the present disclosure.

Referring to FIG. 15, a schematic depicting a system for controlling the solder point and/or junction point temperature of light emitting diode 46 is depicted. Controller 200 is provided and receives a user switch input indicative of a desired brightness of light emitting diode 46. The switch may include a potentiometer that provides a variety of user brightness settings, either at discrete intervals or continuously. The user switch provides a variable current input to the controller 200 based on its setting by the user. Controller 200 also receives a solder point temperature $T_{sp}$ from thermistor or thermocouple 50 (FIG. 6) that is configured to measure the solder point temperature (or the temperature of a thermally conductive paste if one is used). Controller 200 supplies a forward drive current $I_f$ to the light emitting diode 46, the level of which corresponds to the position of the user switch. Controller 200 also supplies a variable drive voltage $V_d$ to fan 26, the value of which corresponds to the speed of rotation of fan blades 52 (FIG. 2), and ultimately, the rate of air drawn into housing intake vents 40a-40i and expelled from fan exhaust vents 41a-41c (FIG. 1).

In the example of FIG. 15, a nominal solder point temperature database 202 is provided. As illustrated by the table in FIG. 16, the nominal solder point temperature database 202 relates light emitting diode forward drive current values ($I_f$) 208 to desired (nominal) solder point temperatures 210. In certain examples, including FIG. 16, the nominal solder point temperature database 202 also relates light emitting diode forward drive current values 208 to the values of user switch settings 206. The user switch may be located in a hip pack or on housing 22 and may be configured with a plurality of detents that provide an audible and/or visual indication of the desired brightness level to the user. The user switch may also comprise a potentiometer that provides a variable input signal to controller 200 so that the controller 200 is aware of the switch position. Database 202 relates the switch positions 206 to forward drive current values 208. In one example, controller 200 sends small current through the potentiometer circuit, and reads the potentiometer setting. Controller 200 then selects the forward drive current 208 corresponding to the detected potentiometer setting (which corresponds to the user switch values in FIG. 16), and generates the selected forward drive current, which is then transmitted to light emitting diode 46.

Based on the forward drive current 208 corresponding to the detected user switch setting 206, controller 200 executes computer readable program instructions stored on a non-transitory computer readable medium, which cause the controller 200 to select a desired solder point temperature 210. The desired (nominal) solder point temperature is compared to the solder point temperature reading ($T_{sp}$) received by controller 200. Using an appropriate control algorithm (e.g., proportional, proportional integral, proportional integral derivative), controller 200 generates a fan drive voltage $V_d$ to adjust the rotation of fan blades 52 (FIG. 2). The control algorithm may be programmed in firmware or software executed by a processor in controller 200. In certain examples, the execution of the control algorithm causes the controller 200 to adjust the fan drive voltage $V_d$ in pre-set increments (e.g., 0.2V/6 seconds). However, it can be continuously adjusted.

Figure 16:
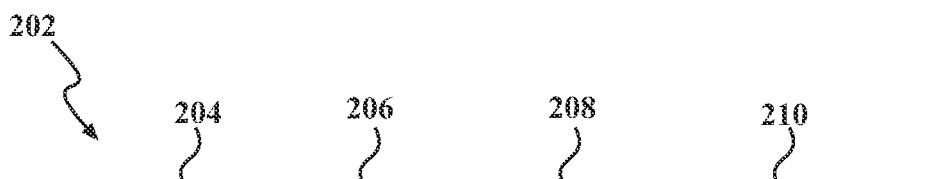
FIG. 16 is a data table from a nominal solder point temperature database.

In preferred examples, the nominal light emitting diode forward drive current values 208 and nominal solder point temperature values 210 in each row correspond to a maximum desired junction temperature $T_j$ specified by the supplier of light emitting diode 46. At a given light emitting diode forward drive current value, equations (1) and (2) may be used to determine a nominal solder point temperature from a desired junction temperature. In the example of FIG. 16, each row and index number 204 correspond to the same desired junction temperature.

A method of generating nominal solder point temperature database 202 will now be described. In accordance with the method, a lighting apparatus is provided which comprises a housing, a light emitting diode, and a fan. In certain examples, the lighting apparatus is apparatus 20. A desired light emitting diode lifetime is selected, and based on the selected lifetime, a desired junction temperature $T_j$ is selected. In one example, the selected L70 lifetime is 3000 hours at maximum forward light emitting diode drive current, yielding a desired junction temperature of 140° C. In another example, the selected L70 lifetime is 7,000 hours at the maximum forward light emitting diode drive current, and the desired junction temperature is 120° C. L70 is an industry standard for the duration of time until the LED light output has decreased to 70% of its initial light output. In accordance with the method, the maximum forward light emitting diode drive current is supplied to the diode, and the rotational speed of the fan is adjusted until a calculated value of the junction temperature (as determined from the measured solder point temperature $T_{sp}$ and the light emitting diode forward drive current $I_f$) is substantially equal to the desired junction temperature. The noise generated by the fan is assessed at the adjusted rotational speed to determine if it is excessive. The desired selected junction temperature is then adjusted, and the rotational speed of the fan is adjusted to a level just below that where the fan noise exceeds a desired level. The value of the junction temperature when the fan noise is substantially equal to the desired level of noise is the nominal operating junction temperature that is used. Using this nominal junction temperature value and a plurality of forward light emitting diode drive current values, a plurality of nominal solder point temperature values are calculated from equations (1) and (2), wherein each nominal solder point temperature corresponds to a forward light emitting diode drive current value. In some cases, fan noise is assessed qualitatively by listening to the fan and determining whether the noise is acceptable or excessive. In other cases, fan noise may be assessed with a sound meter by comparing a sound meter reading to a selected decibel level.

A modified version of the temperature control scheme of FIGS. 15 and 16 will now be described. The control scheme is represented diagrammatically as shown in FIG. 15, except that controller 200 does not receive an actual solder point temperature measurement ($T_{sp}$) from a thermistor or thermocouple 50 (FIG. 6). Based on the forward light emitting diode drive current $I_f$ corresponding to the detected user switch setting, controller 200 executes computer readable program instructions stored on a non-transitory computer readable medium, which cause the controller 200 to select a desired fan drive voltage $V_d$. In addition, in this modified control scheme, the solder temperature control database 202 of FIG. 15 is replaced with fan drive voltage $V_d$ database 203. Thus, the fan drive voltage $V_d$ is regulated, but its value is not re-set or adjusted based on a measured value of the solder point temperature $T_{sp}$.

In accordance with one method, the user adjusts a user switch on a hip pack or on housing 22 to achieve a desired brightness. The controller 200 supplies a forward drive current $I_f$ to the light emitting diode 46 based on the position of the user switch. Fan drive voltage $V_d$ database 203 relates fan drive voltage $V_d$ values to drive current $I_f$ values. Using the database 203 (not shown in FIG. 15), controller 200 selects and provides the desired value of the fan drive voltage $V_d$ to the fan 26.

Figure 17:
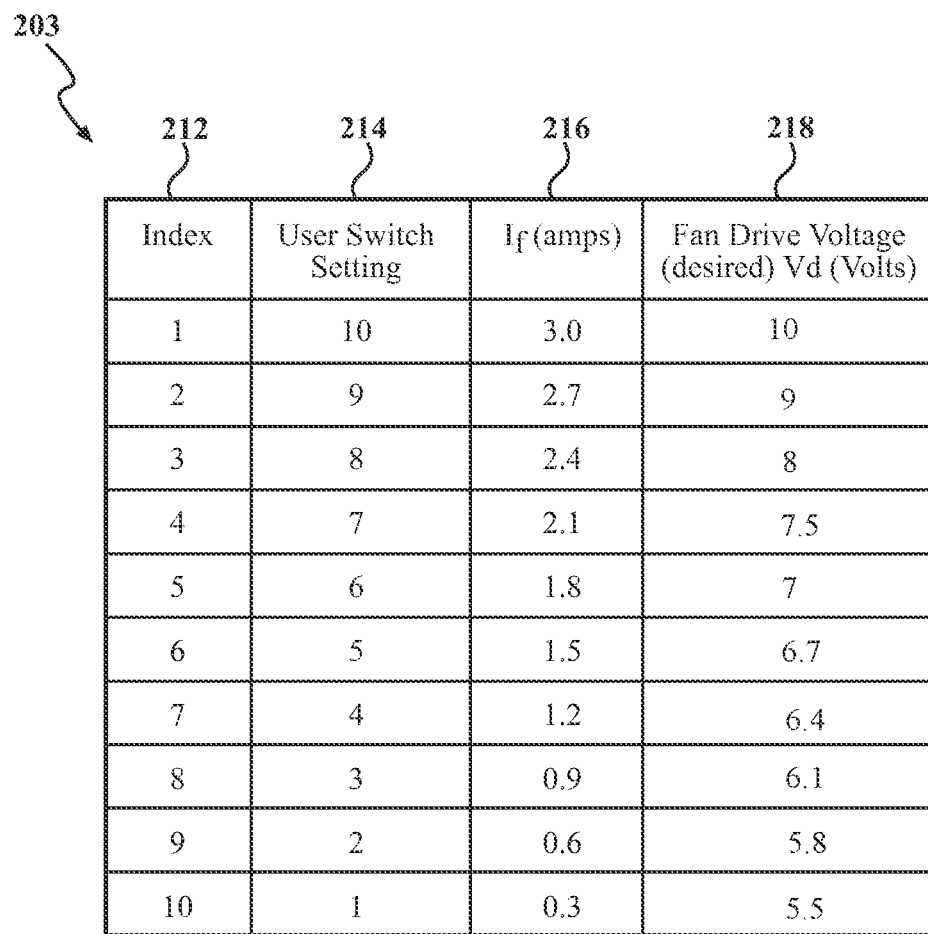
FIG. 17 is a data table from a nominal fan drive voltage database.

Referring to FIG. 17, fan drive voltage database 203 includes an index 212 and fields for a user switch setting 214, a light emitting diode forward drive current $I_f$, 216 and a desired fan drive voltage 218. Each value of index 212 defines a specific set of user switch setting values, light emitting diode forward drive current $I_f$ values, and fan drive voltage $V_f$ values. The user switch may comprise a potentiometer that provides a variable input signal to controller 200 so that controller 200 is aware of the switch position. Controller 200 selects the desired fan drive voltage $V_d$ 218 that corresponds to the light emitting diode forward drive current $I_f$ value 216 and supplies the selected drive voltage to the fan 26.

A method of generating the fan voltage database 203 of FIG. 17 will now be described. In accordance with the method, a lighting apparatus is provided which comprises a housing, a light emitting diode, and a fan. In certain examples, the lighting apparatus is apparatus 20. A desired light emitting diode lifetime is selected, and based on the selected lifetime, a desired junction temperature $T_j$ is selected. In one example, the selected L70 lifetime is 3000 hours at the maximum forward light emitting diode drive current, yielding a desired junction temperature of 140° C. In another example, the selected L70 lifetime is 7,000 hours at the maximum forward light emitting diode drive current, and the desired junction temperature is 120° C. The method is preferably carried out at the maximum common ambient temperature, which is from about 85° F. to about 90° F. in certain examples. In accordance with the method, the maximum forward light emitting diode drive current is supplied to the diode 46, and the fan drive voltage $V_d$ (and, hence, the rotational speed of the fan) is adjusted until a calculated value of the junction temperature (as determined from the measured solder point temperature $T_{sp}$ and the light emitting diode forward drive current $I_f$) is substantially equal to the desired junction temperature $T_j$. The noise generated by the fan is assessed at the adjusted fan drive voltage $V_d$ to determine if it is excessive. If the noise is excessive, the selected lifetime is reduced, and the corresponding junction temperature (which will be higher) is determined. In some cases, fan noise is assessed qualitatively by listening to the fan and determining whether the noise is acceptable or excessive. In other cases, fan noise may be assessed with a sound meter by comparing a sound meter reading to a selected decibel level. The light emitting diode forward drive current $I_f$ is then adjusted to the various values in column 216, and the fan drive voltage $V_d$ is adjusted to achieve the desired junction temperature $T_j$ at each value of the drive current $I_f$. The resulting fan drive voltage $V_d$ values are stored in column 218.

Referring to FIGS. 8A-8D and 9, in accordance with the seventh aspect of the present disclosure, a lighting apparatus is provided which comprises a light emitting diode and a switch operatively connected to the light emitting diode, wherein the switch is removably attachable to a surgical scrub and is operable to adjust the operation of the light emitting diode. Lighting apparatus 20 is connected to a head band 93. A conduit 92 carries a plurality of wires from a hip pack 90 to head band 93, and around to lighting apparatus 20. In another embodiment, although not visible, head band 93 includes internal conduits through which the wires are routed to electrically connect the light emitting diode 46 and the fan 26 to components in the hip pack 90.

Hip pack 90 includes controller 200 (FIG. 15) and a user switch for energizing and/or adjusting the brightness (intensity) of light emitting diode 46 in the manner described previously. In general, the hip pack 90 is considered to be outside of the surgeon's sterile field. Thus, the surgeon needs to have an assistant manipulate switches contained on or in the hip pack 90. However, this is inefficient, and it would be undesirable to have the surgeon contact the hip pack during a surgical procedure.

Figure 8A:
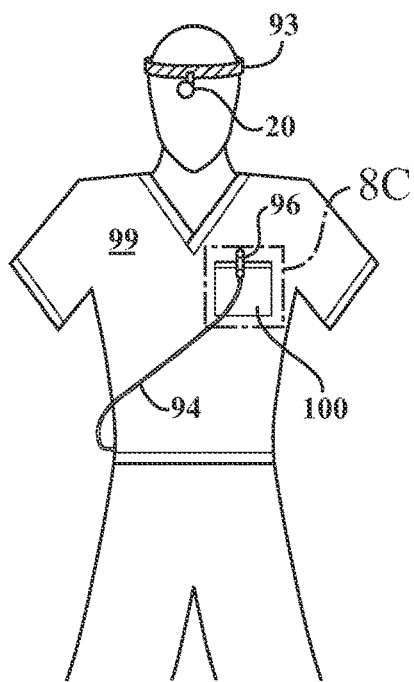
FIG. 8A is a front elevational view of undergown switch removably attached to a chest pocket of a surgeon's surgical scrub.
Figure 8B:
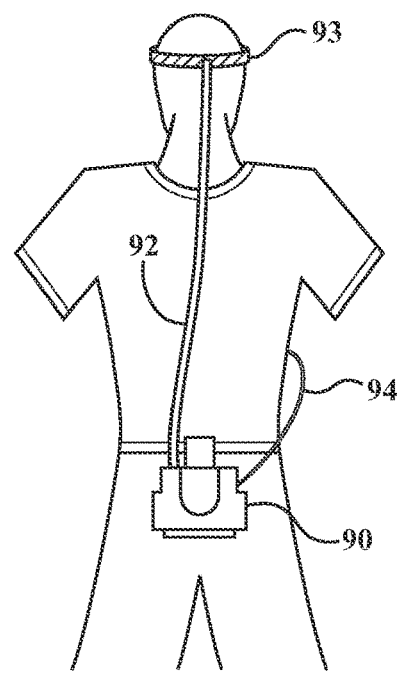
FIG. 8B is a rear elevational view of FIG. 8A showing a surgeon wearing the lighting apparatus of FIG. 1 and a hip pack connected to a surgical scrub pocket switch.
Figure 8C:
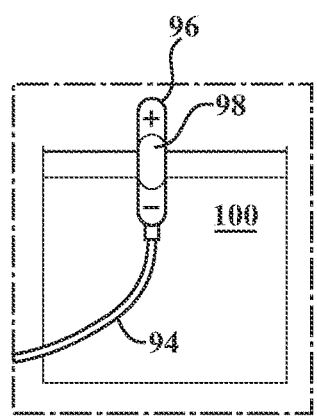
FIG. 8C is a close-up view of the undergown switch of FIG. 8B.

Undergown switch 96 is provided which is attachable to the surgeon's surgical scrub 99 pocket 100 as shown in FIG. 8A. In the preferred embodiment seen in the example of FIG. 8C, the switch 96 includes one or more discrete buttons 98 in this case seen as "+," "center," and "−," that each send a unique signal to controller 200. Controller 200 can interpret each unique signal and adjust output to the light emitting diode as dictated by its programming. It is understood that switch 96 may be any variant of switch or potentiometer that enables adjustment of the operation of the light emitting diode. For further illustration of switch variation, switch 98 can be a slide potentiometer that slides between two end positions to vary a signal transmitted to the controller 200 via switch conduit 94, which includes one or more wires that electrically connect the switch 96 and the controller 200. It is also understood that the switch 96 may be used to signal the controller 200 as previously described, or in another embodiment switch 96 can be used to directly control the current or voltage of the light emitting diode. Switch 96 may also be depressible, slidable, capacitive, or manipulable in other ways to affect the operation of lighting apparatus 20.

Although not visible in the figures, the switch 96 preferably includes a clip that facilitates attachment of switch 96 to scrub pocket 100. In preferred examples, switch 96 is used in conjunction with a primary switch provided in hip pack 90. In such examples, if switch 96 is disconnected from light emitting diode 46, the primary switch in hip pack 90 will become operative to energize and de-energize light emitting diode 46 and/or to control the drive current supplied to it.

It is also understood that the switch 96 can be attached to any other part of the body or gown as desired by the user, provided it does not risk contamination of the sterile field.

Figure 8D:
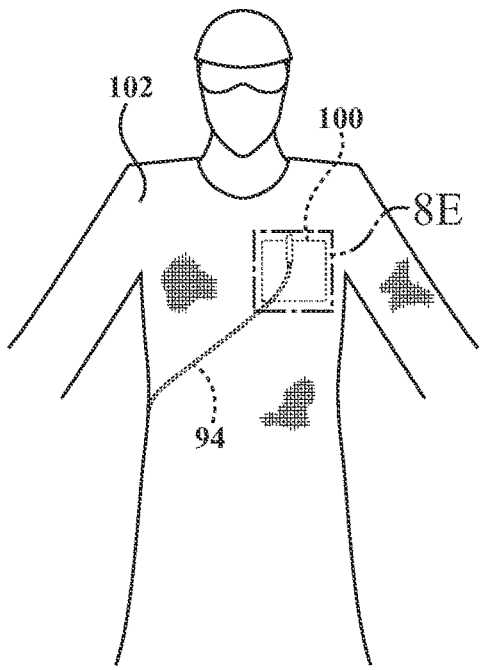
FIG. 8D is a front elevational view of the surgeon of FIGS. 8A-8C wearing a gown over the undergown switch.
Figure 9:
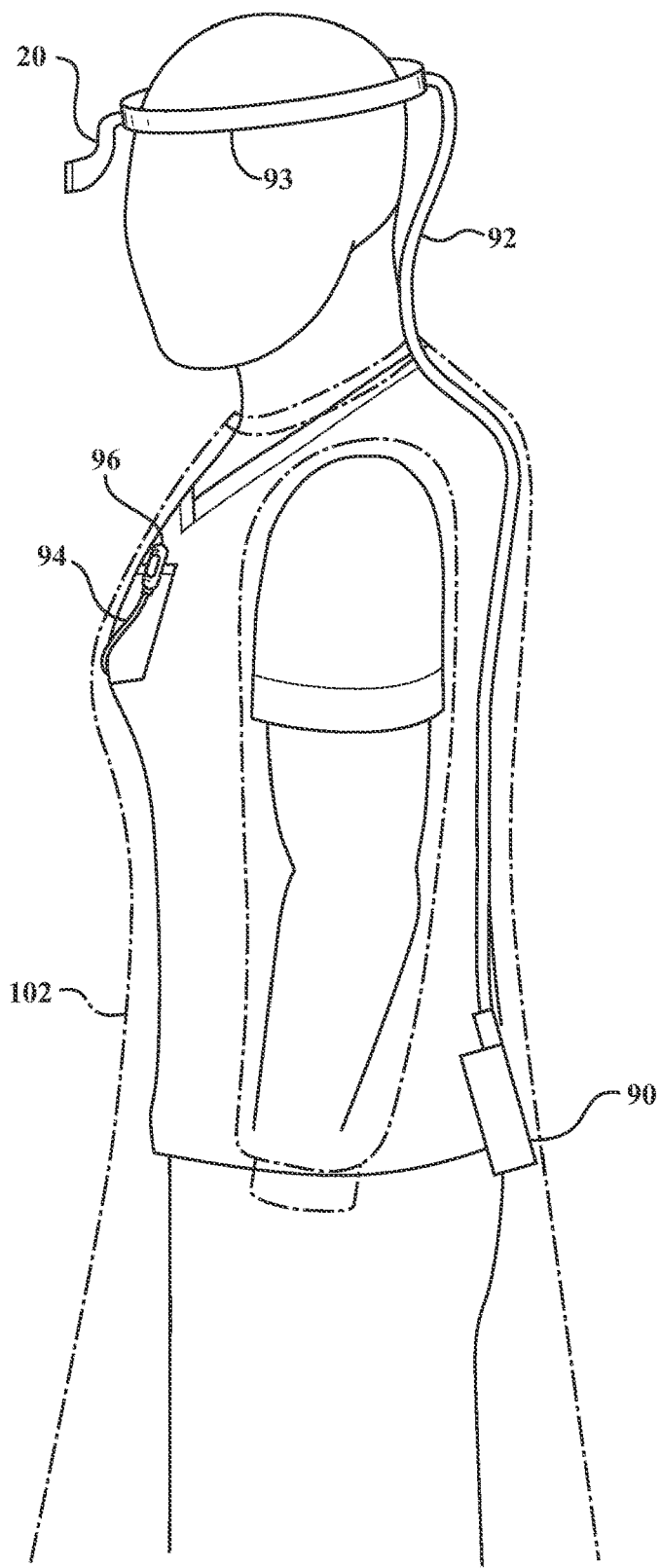
FIG. 9 is a side view of a surgeon wearing a surgical gown over the undergown switch of FIG. 8A.

As shown in FIG. 8D, during surgery the surgeon will attach switch 96 to scrub 99 and don a surgical gown 102 that is worn over the surgical scrub 99 so that an outside surface of gown 102 is exposed and an inside surface of gown 102 faces the surgeon's body. The portion of the surgical gown 102 that is over the scrub pocket 100 lies within the sterile field. The switch 96 is configured so that the surgeon can manipulate button 98 through a portion of gown 102 which is in the sterile field, allowing the surgeon to adjust the operation of lighting apparatus 20 with a gloved, sterile hand that remains in the sterile field. In some examples, the surgeon uses switch 96 to selectively provide power to light emitting diode 46. In the same or other examples, the surgeon uses the switch 96 to selectively adjust the brightness (intensity) of the light emitting diode 46, such as by adjusting the forward light emitting diode drive current. In other examples, switch 96 may be configured to allow the surgeon to adjust other functions of auxiliary equipment in control of the microcontroller housed in hip pack 90, for example the speed of fans within the personal cooling apparatus as described below.

Figure 10A:
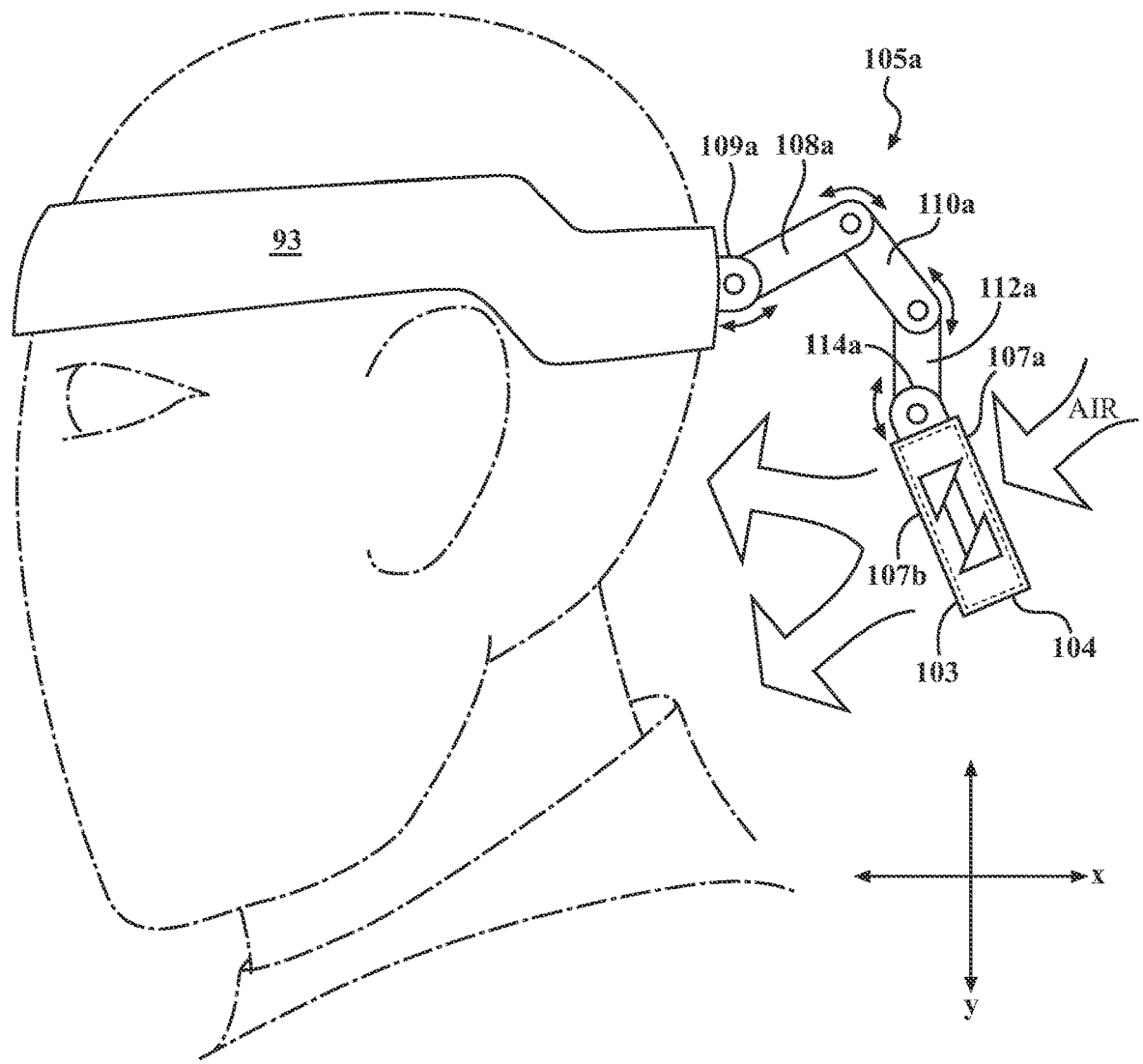
FIG. 10A is a side elevational view of an auxiliary fan system attached to a surgeon's head.
Figure 10B:
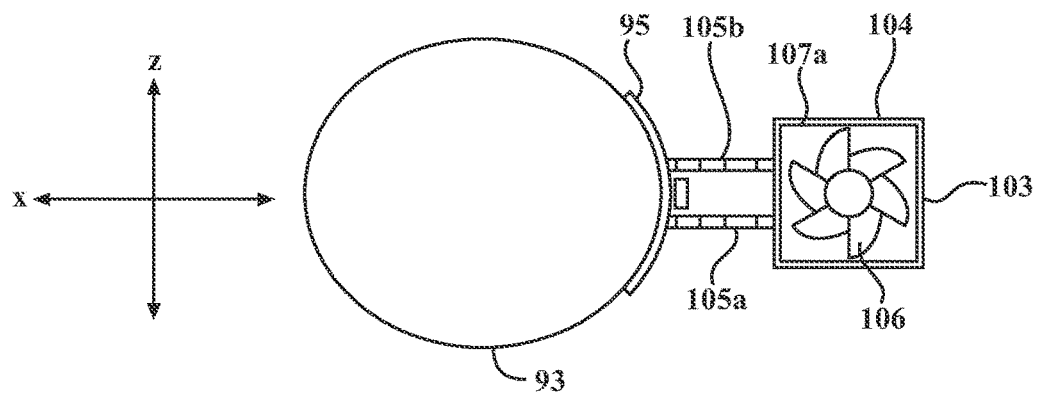
FIG. 10B is a top plan view of the auxiliary fan system of FIG. 10A.

In accordance with the eighth aspect of the present disclosure, a personal cooling apparatus is provided which includes a head band and a fan module connected to the head band. Referring to FIGS. 10A-C, an embodiment of a personal cooling apparatus is depicted. The personal cooling apparatus comprises a head band 93 and fan module 103. In certain examples, the orientation of the fan module 103 relative to the head band 93 is adjustable. In the same or other examples, the position of the fan module 103 relative to the head band is adjustable along a first axis and/or a second axis.

Fan module 103 includes a housing 104 with an intake opening 107a and an exhaust opening 107b. Fan blades 106 rotate to draw air in through intake opening 107a and exhaust air through exhaust opening 107b. The personal cooling apparatus further comprises a first articulating assembly 105a and second articulating assembly 105b. First articulating assembly 105a includes first articulating arm 108a, second articulating arm 110a, and third articulating arm 112a. A first end of first articulating arm 108a is connected to a first bracket 109a which is attached to head band 93. A second end of first articulating arm 108a is connected to a first end of second articulating arm 110a. A second end of second articulating arm 110a is connected to a first end of third articulating arm 112a. A second end of first articulating arm 112a is connected to a bracket 114a mounted on housing 104 of fan module 103. As shown in FIG. 10A, first articulating arm 108a is pivotable about its point of connection to head band bracket 109a. Second articulating arm 110a is pivotable about its point of connection to first articulating arm 108a. Third articulating arm 112a is pivotable about its point of connection to second articulating arm 110a. Fan module 103 is pivotable about its point of connection to third articulating arm 112a. Second articulating assembly 105b is configured similarly, with articulating arms 108b, 110b, and 112b, head band bracket 109b, and fan module bracket 114b (not shown in figures) being configured in parallel fashion to articulating arms 108a, 110a, and 112a, head band bracket 109a, and fan module bracket 114a. As shown in FIG. 10A, the personal cooling assembly allows the fan module 103 to be repositioned at various distances from head band 93 and a user's head along a first (x) axis and at various distances from head band 93 and the top of a user's head along a second (y) axis. In certain examples, the fan module 103 is also pivotable about a third (z) axis that is perpendicular to the first and second axes, allowing a user to adjust the orientation of the plane in which fan blades 106 rotate relative to head band 93. In preferred examples, the articulating arms 108a/b, 110a/b, and 112a/b and the brackets 109a/b and 114a/b are configured to allow for indexed rotation and movement such as by providing knobs or other fasteners that can be loosened and tighten to securely and selectively reposition the fan module 103 relative to the head band along first and second axes x and y and, in certain examples, about third axis z.

In the example of FIGS. 10A-C, the fan module 103 draws in air that is away from the user and exhausts air toward the user. However, in certain examples, the direction of rotation of fan blades 106 is reversible, allowing the fan module 103 to draw in air from between the fan module 103 and the user and to exhaust air in a direction away from the user. As shown in FIGS. 10B-C, the head band 93 may be made out of a suitable cloth or plastic and may include a reinforced section of metal or plastic 95 which stabilizes the fan module and articulating assemblies 105a and 105b. Knob 97 is provided for tightening and loosening the head band via a ratchet mechanism integrated in to the head band 93. In certain examples, the ratchet mechanism is a standard feature of surgical head bands known to those skilled in the art. In the same or other examples, the fan module 103 may be removably connected to the reinforced section of metal or plastic 95 by one or more fasteners, or similarly may be removably connected to head band 93 by one or more fasteners. In certain examples, the speed and/or direction of rotation of the fan blades 106 is user adjustable. In the same or other examples, user adjustability is provided via the undergown switch 96 of FIGS. 8A-D and 9, via an in-line switch between the fan module 103 and a power source, or via a switch integrated in to the fan module 103 itself, to name a few examples.

Referring to FIG. 11, another example of a personal cooling apparatus is depicted. The personal cooling apparatus includes a head band 93 configured as in the example of FIGS. 10A-10C. The personal cooling apparatus also includes a first fan module 103 and a second fan module 116. The first fan module 103 is substantially similar to the fan module 103 of FIGS. 10A-10C and is connected to head band 93 by first and second articulating assemblies 105a and 105b similar to those of FIGS. 10A-10C. However, second fan module 116 is connected to brackets (not shown) on the housing 104 of first fan module 103. The side of the fan module housing 104 to which second fan module 116 is connected is opposite the side of the fan module housing 104 to which the first and second articulating assemblies 105a and 105b are connected. Third and fourth articulating assemblies 122a and 122b connect the first and second fan modules 103 and 116 to one another and are configured similarly to first and second articulating assemblies 105a and 105b. Thus, second fan module 116 is movable along a first (x) axis and a second (y) axis relative to first fan module 103 and relative to head band 93. In certain examples, second fan module 116 is also pivotable about a third (z) axis relative to the first fan module 103, allowing a user to adjust the rotational orientation of the plane in which fan blades 118 rotate relative to the first fan module 103 and the head band 93.

Second fan module 116 includes a housing 120 having an intake side and an exhaust side and fan blades 118. In certain examples, the fan blades 118 may be rotated in two directions, allowing the direction of air flow through the fan module 116 to be selectively reversed. In certain examples, controls for operating the fan modules 103 and/or 116 are provided in a hip pack such as hip pack 90 (FIG. 8D). In other examples, an undergown switch 96 is provided to allow a surgeon to adjust the speed of rotation of the fan blades 106 and 118 and/or to change the direction of rotation of fan blades 106 and 118. In certain examples, the speed and/or direction of rotation of the fan blades 106 and 118 is user adjustable. In the same or other examples, user adjustability is provided with the undergown switch 96 of FIGS. 8A-D and 9, via an in-line switch between the fan module 103 and a power source, or via a switch integrated in to the fan module 103 itself, to name a few examples. Suitable switches include on/off switches, or continuously variable or stepped rotary and slide potentiometers.

Alternatively, power and control circuitry may be provided remotely via a tether cable from a wall DC power adapter, or the fan modules 103 and 116 may be run from batteries and control circuitry affixed to or in head band 93. In a preferred example, power is supplied via a power source located in a hip pack 90 (FIGS. 8A-D and 9) and an auxiliary cable connected to the power source and the fan modules 115 and 116.

Referring to FIG. 12, a personal cooling apparatus comprising a head band 93 and an array of fan modules is depicted. The array of fan modules includes first fan module 103, second fan module 116, third fan module 123, and fourth fan module 128.

The first and second fan modules 103 and 116 are configured as described previously, with a first side of the first fan module housing 104 being connected to head band 93 and a second side of the fan module housing 104 being connected to second fan module 116. Third fan module 123 includes a housing 126 with an intake opening and an exhaust opening and fan blades 124. Fourth fan module 128 includes a housing 132 with an intake opening, an exhaust opening and fan blades 130.

Third fan module 123 is connected to a third side of the first fan module housing 104, and fourth fan module 128 is connected to a fourth side of the first fan module housing 104, wherein the third and fourth sides of the first fan module housing are opposite one another. Third fan module 123 is connected to the third side of the first fan module housing 104 via fifth and sixth articulating assemblies 136a and 136b. Fourth fan module 128 is connected to the fourth side of the first fan module housing 104 via seventh and eight articulating assemblies 134a and 134b. The fifth, sixth, seventh, and eighth articulating assemblies 134a, 134b, 136a, and 136b may include three articulating arms as in the case of first and second articulating assemblies 105a, 105b and third and fourth articulating assemblies 122 and 122b. However, in the example of FIG. 12, the fifth, sixth, seventh, and eight articulating assemblies 134a, 134b, 136a, and 136b only include two articulating arms each. Third fan module 123 is movable relative to the first fan module 103 along both the y and z axis and is rotatable about the x-axis relative the first fan module. Fourth fan module 128 is movable relative to the first fan module 103 along both the y and z axes and is rotatable about the x-axis relative to the first fan module 103. In the illustrated example, third and fourth fan modules 123 and 128 are not movable along the x-axis relative to the first fan module 103. Similarly, second fan module 116 is not movable along the z-axis relative to the first fan module 103. Otherwise, second fan module 116 is movable and rotatable relative to first fan module 103 as described previously with respect to FIG. 11. In certain examples, the speed and/or direction of rotation of the fan blades 106, 118, 124, and 130 is user adjustable. In the same or other examples, user adjustability is provided with the undergown switch 96 of FIGS. 8A-D and 9. In the depicted examples of FIGS. 8A-8D and 9-12, the fan modules 103, 116, 123, and 128 intake and exhaust ambient air. However, in other examples, they may intake heated and/or cooled air from a secondary heating or cooling source. In certain examples, any of the fan module configurations of FIGS. 10A-C, 11, and 12 may be used with lighting apparatus 20, and the fans may be manipulated by a controller such as controller 200 (FIG. 15) based on a suitable signal.

Referring to FIGS. 13A-13D, a personal cooling apparatus is provided which comprises a head band 93 and a fan module 139 that is integrated into the head band 93. The head band includes one or more internal conduits 146 that define a lumen 147. Fan module 139 includes a housing 144 and fan blades 142. The head band 93 is attached to each of two opposing sides of housing 144. Thus, the fan module 139 is not movable relative to the head band 93. The fan module 139 has an air intake that is exposed and an exhaust that discharges into conduit 146. However, in certain examples, the rotational direction of fan blades 142 may be varied to draw in air from conduit 146 and exhaust it to the atmosphere.

A close up view of a section of head band 93 is provided in FIGS. 13C and 13D. Head band 93 includes a cloth section 140 which may comprise natural or synthetic materials, for example, cotton or neoprene. Cloth section 140 is preferably formed from a material that provides padding and wicking to remove moisture from the surgeon's head. Conduit 146 is preferably made of flexible plastic and is positioned in or on top of a channel defined between supports 138a and 138b. The supports 138a and 138b are preferably made of plastic and provide structural integrity to the head band 93 as well as stabilization for conduit 146. Conduit 146 can include a plurality of exhaust openings 148a-148i for exhausting air circulated by fan module 139 to locations around the surgeon's head (additional exhaust openings are provided on the side of head band 93 which is not visible in FIG. 13A). The conduit may be configured as a full cylindrical tube, or as a semi-cylindrical tube with the cloth section 140 effectively acting as a wall of the conduit 146 (FIGS. 13C and 13D), allowing air in the conduit to facilitate in the evaporation of moisture collected in cloth section 140. The power supply and controls for fan module 139 may be configured as described previously for fan modules 103, 116, 123, and 128.

Figure 13E:
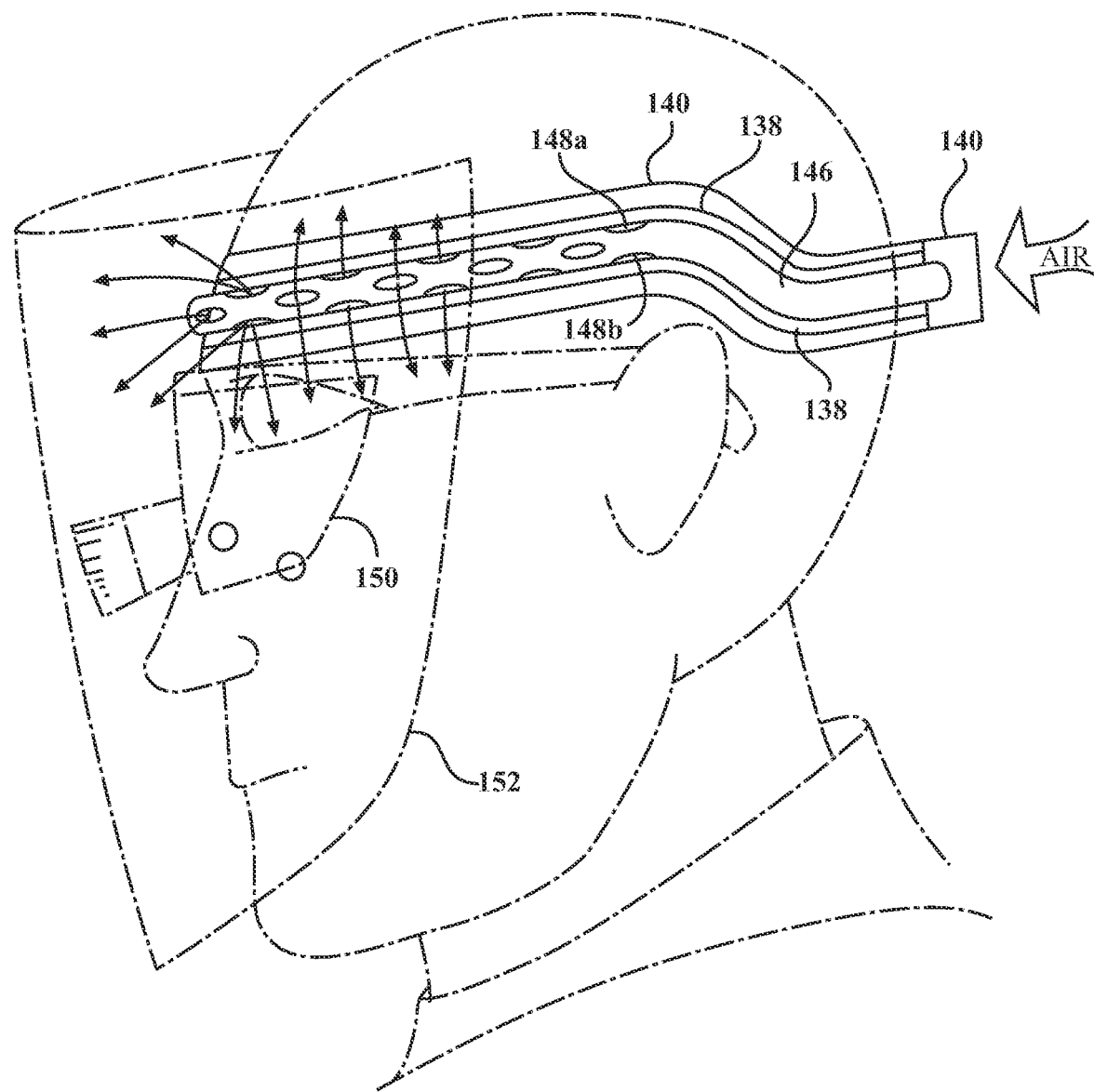
FIG. 13E is a side elevational view of the auxiliary fan apparatus of FIG. 13A worn with a visor and glasses.

Referring to FIG. 13E, in certain examples, the personal cooling apparatus of FIGS. 13A-13D may be beneficially used with eyewear such as loops 150 and/or a face shield 152. The surgeon's breath or sweat may tend to fog the shield 152 and/or loops 150. Thus, fan module 139 can be operated to circulate fresh air through conduit 146 and into the region between the surgeon's face and shield 152 to reduce such fogging.

Figure 14:
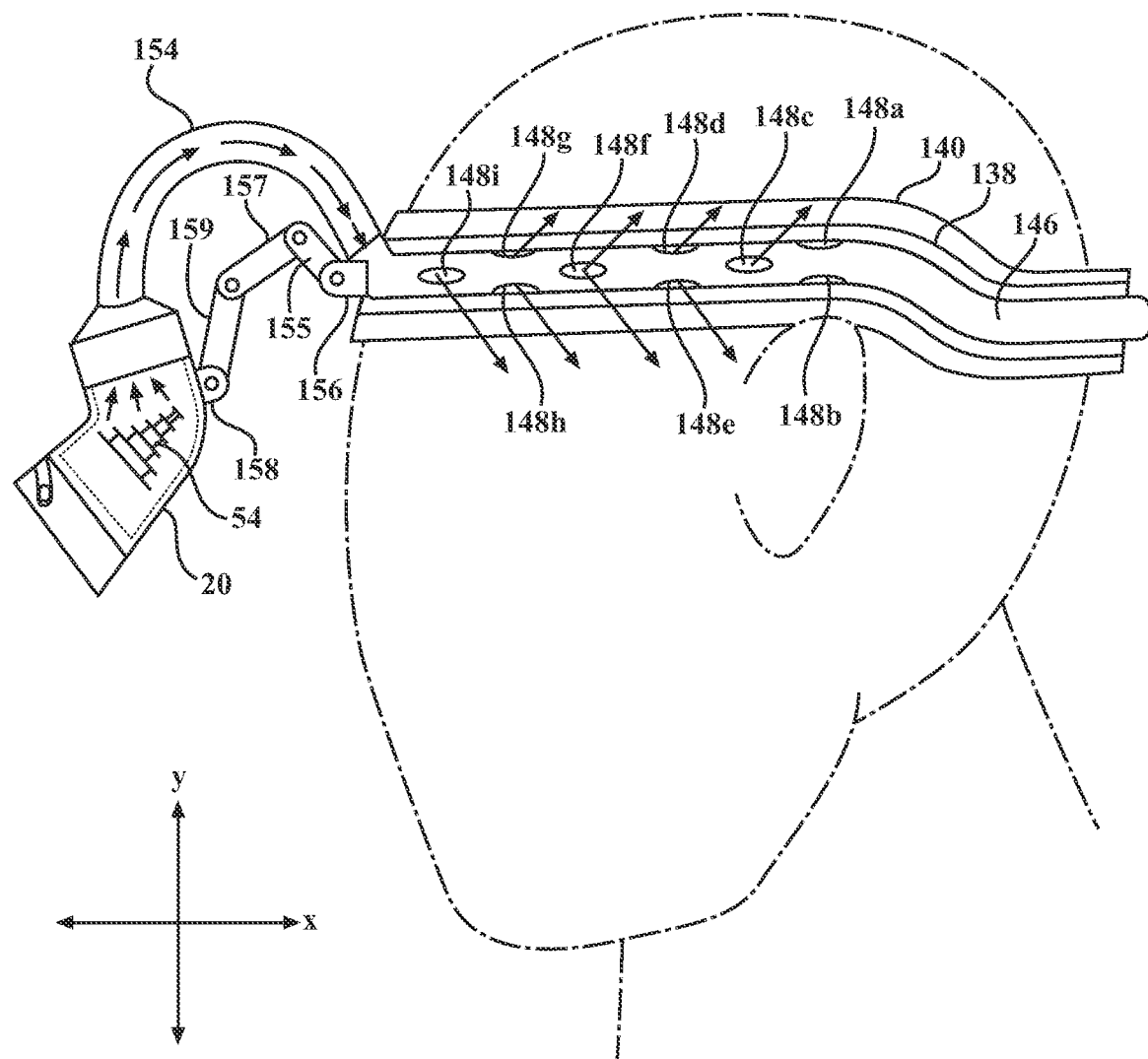
FIG. 14 is a side elevational view of a vented lighting apparatus comprising the lighting apparatus of FIG. 1 and the auxiliary fan apparatus of FIG. 13A.

Referring to FIG. 14, a lighting apparatus 20 is connected to a head band 93 configured similarly to the head band 93 of FIGS. 13A-13D. However, in this example, there is not necessarily a separate fan unit integrated into head band 93. Instead, the exhaust openings 41a-41c of fan 26 (FIG. 1) are connected to an exhaust conduit 154 which is connected to and in fluid communication with the interior of head band conduit 146. Heated air from lighting apparatus 20 is discharged into exhaust conduit 154 and flows into head band conduit 146, eventually exiting the head band conduit 146 at exhaust openings 148*a*-148*i*. Conduit 154 is preferably formed from a flexible plastic tubing. Lighting apparatus housing 22 includes a bracket 158, and head band 93 includes a bracket 156. A first end of first articulating arm 155 is connected to head band bracket 156. A second end of first articulating arm 155 is connected to a first end of second articulating arm 157. A second end of second articulating arm 157 is connected to a first end of third articulating arm 159. A second end of third articulating arm 159 is connected to lighting apparatus bracket 158. First articulating arm 155 is pivotable about its point of connection with head band bracket 156. Second articulating arm 157 is pivotable about its point of connection with first articulating arm 155. Third articulating arm 159 is pivotable about its point of connection with second articulating arm 157 and its point of connection with lighting apparatus bracket 158. Thus, lighting apparatus 20 is movable along a first (x) axis relative to head band 93 and along a second (y) axis relative to head band 93. Lighting apparatus 20 is rotatable about a third (z) axis that is perpendicular to the first (x) and second (y) axes relative to the head band 93. Although not shown, lighting apparatus 20 can be movable along the third (z) axis facilitated by a joint allowing such movement at 156. The lighting apparatus 20 and head band 93 of FIG. 14 beneficially allow heat generated by lighting apparatus 20 to be moved away from the surgeon's forehead to provide increased comfort.

In certain preferred examples, the light emitting diode 46 and fan 26 of lighting apparatus 20 are battery powered. Rechargeable batteries are preferred, and batteries comprising lithium ion fuel cells are especially preferred. During surgical procedures, it is beneficial for the surgeon to be made aware if the battery is about to reach a specified charge capacity, such as the end of life. Visual indications are undesirable because they require the surgeon to periodically look away from the surgical field to ascertain the battery's charge capacity. Audible indications can be distracting or ineffectual if the surgical theater is too loud. In certain cases, multiple surgeons, each with his or her own lighting apparatus 20, may be present in the same surgical theatre, resulting in confusion as to whose battery capacity alarm is sounding if audible battery life indications are used.

Figure 18:
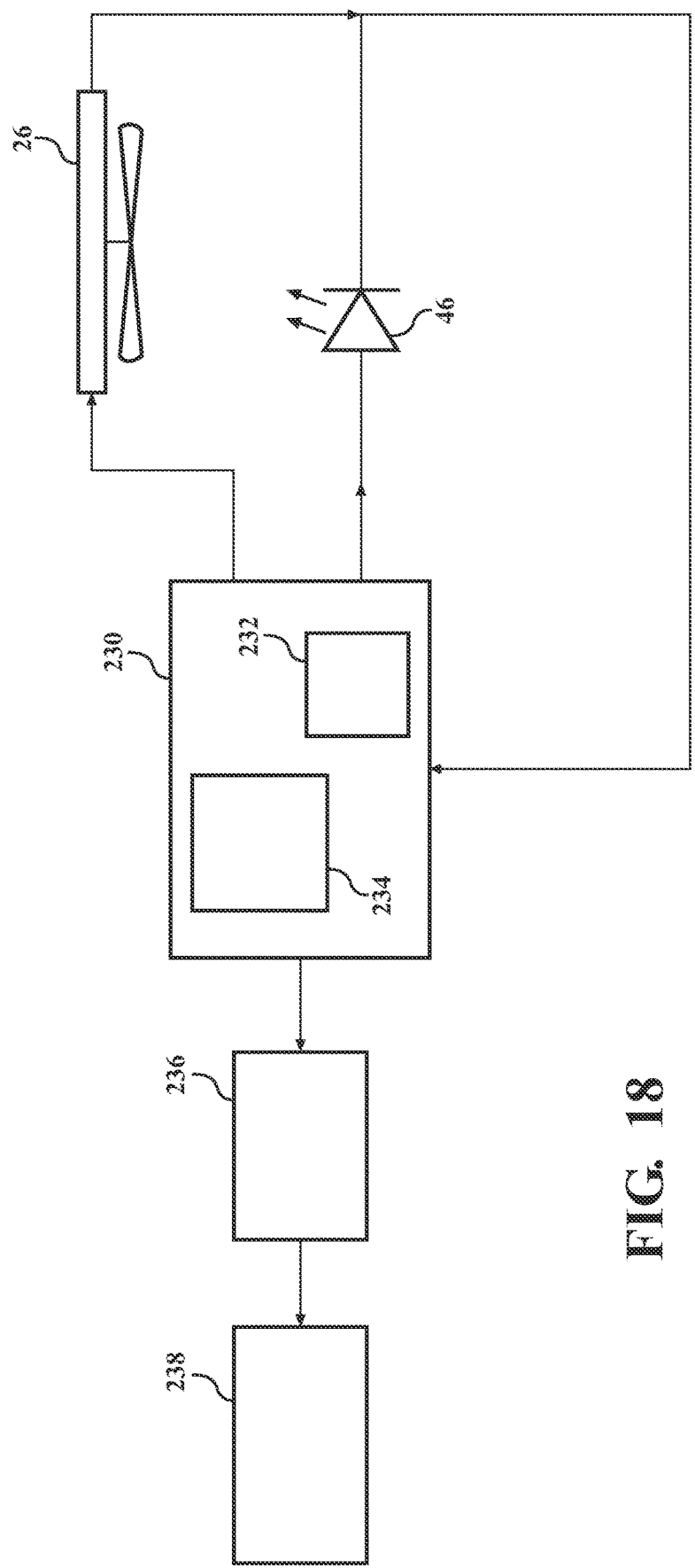
FIG. 18 is diagram of a lighting system comprising a lighting apparatus, a battery system, and a battery capacity detection controller, and a vibrating motor for providing a haptic indication of the remaining battery capacity.

To address the foregoing issues, a lighting apparatus is provided which uses haptic communication to alert the surgeon that the battery will soon reach a specified charge capacity, such as end of life. In one preferred example, the lighting apparatus comprises a vibrating motor. The vibration of the motor is felt by the surgeon and alerts him or her to the charge capacity, which may be represented as a percentage of the full charge (e.g., 10 percent of full charge) or the time remaining until the charge capacity reaches a specified value (e.g., 10 minutes to end of life) at some measured or calculated rate of discharge (which may be dynamically calculated). Referring to FIG. 18, a lighting system is depicted which comprises a light emitting diode 46 and a fan 26, which may be provided as part of lighting apparatus 20 (described previously). Battery system 230 comprises at least one fuel cell 232, which is preferably an array of lithium ion fuel cells. A fuel cell capacity circuit 234 is also provided. The fuel cell capacity circuit 234 is designed to detect the charge capacity of fuel cells 232 and to provide an output signal indicative of the capacity. In preferred examples, the fuel cell capacity circuit 234 provides an output signal indicative of the total remaining charge capacity of fuel cells 232 or the time remaining until a specified charge capacity (such as end of life) is reached. The fuel cell capacity circuit 234 is operatively connected to a batter capacity detection controller 236.

One example of a suitable, commercially-available battery system 230 is the NH2054HD34 rechargeable smart lithium ion battery pack supplied by Inspired Energy® of Newberry, Fla. This battery pack includes a fuel cell capacity circuit and lithium ion cells and is programmed to determine the state of charge of fuel cells by integrating the input and output current using impedance tracking to track the battery charge capacity. It also includes an LCD indication for displaying the percentage of the battery charge capacity that is remaining. The NH2054HD34 includes a microprocessor and associated circuitry for communicating with an external host device such as battery capacity detection controller 236 and is programmed to provide a predicted remaining battery life and a rolling average of the predicted remaining battery life for use by the battery capacity detection controller 236.

Battery capacity detection controller 236 preferably includes a printed circuit board, a non-transitory computer readable medium (such as flash memory), a central processing unit (CPU), random access memory (RAM) and a plurality of input and output pins. In one example, the battery capacity detection controller 236 may comprise a microcontroller mounted on a PCB with a plurality of input-output connectors and the microcontroller may include a CPU and on-chip flash memory as the non-volatile storage medium.

In one example, the battery capacity detection controller 236 is programmed to determine the remaining time until fuel cells 232 reach a specified charge capacity, such as end of life, based on the fuel cell capacity circuit 234 output signal that is indicative of the remaining charge capacity of fuel cells 232. In certain examples, the battery capacity detection controller 236 is programmed to determine the rate of charge consumption of fuel cells 232 and to dynamically integrate the fuel cell capacity circuit 234 output signal to predict the time remaining until the fuel cells 232 reach a specified charge capacity, such as end of life. The battery capacity detection controller 236 then transmits a vibration signal to vibrating motor 238 when the predicted remaining time reaches one or more specified values. The vibration signal causes vibrating motor 238 to vibrate, which can be felt by the surgeon. In one example, the battery capacity detection controller 236 is programmed to transmit a vibration signal to vibrating motor 238 when the predicted remaining time to the end of life of the fuel cells is ten (10) minutes, five (5) minutes, and one (1) minute.

In other cases, the battery system 230 may itself provide the predicted time until the fuel cells 232 reach end of life or some specified charge capacity value. For example, the NH2054HD34 provides a variety of messages that can be accessed by battery capacity detection controller 236, including RunTimeToEmpty( ) which indicates the predicted remaining battery life at the present rate of discharge, and AverageTimeToEmpty( ) which indicates the rolling average of the predicted remaining battery life. These messages can be used by battery capacity detection controller 236 and compared to a specified set point or set points to determine when to transmit a vibration signal to vibration motor 238.

Vibrating motor 238 may be provided as a stand-alone item and wired to a PCB, or it may be mounted on the PCB that comprises part of the battery capacity detection controller 236. In the former case, vibrating motor 238 is preferably disposed within hip pack 90 (FIG. 9) and wired to the PCB, which may also be disposed in the hip pack 90.

In the latter case, the battery capacity detection controller 236 PCB with the vibrating motor 238 mounted thereon may be located in hip pack 90. Suitable stand-alone vibrating motors 238 include the K'otl® Z6DL2B0541192 6 mm, 3V vibrating motor. Suitable PCB-mounted vibrating motors 238 include the K'otl® Z6DCBB0056091, which is a 6 mm, 3V vibrating motor with PCB pins.

Figure 19A:
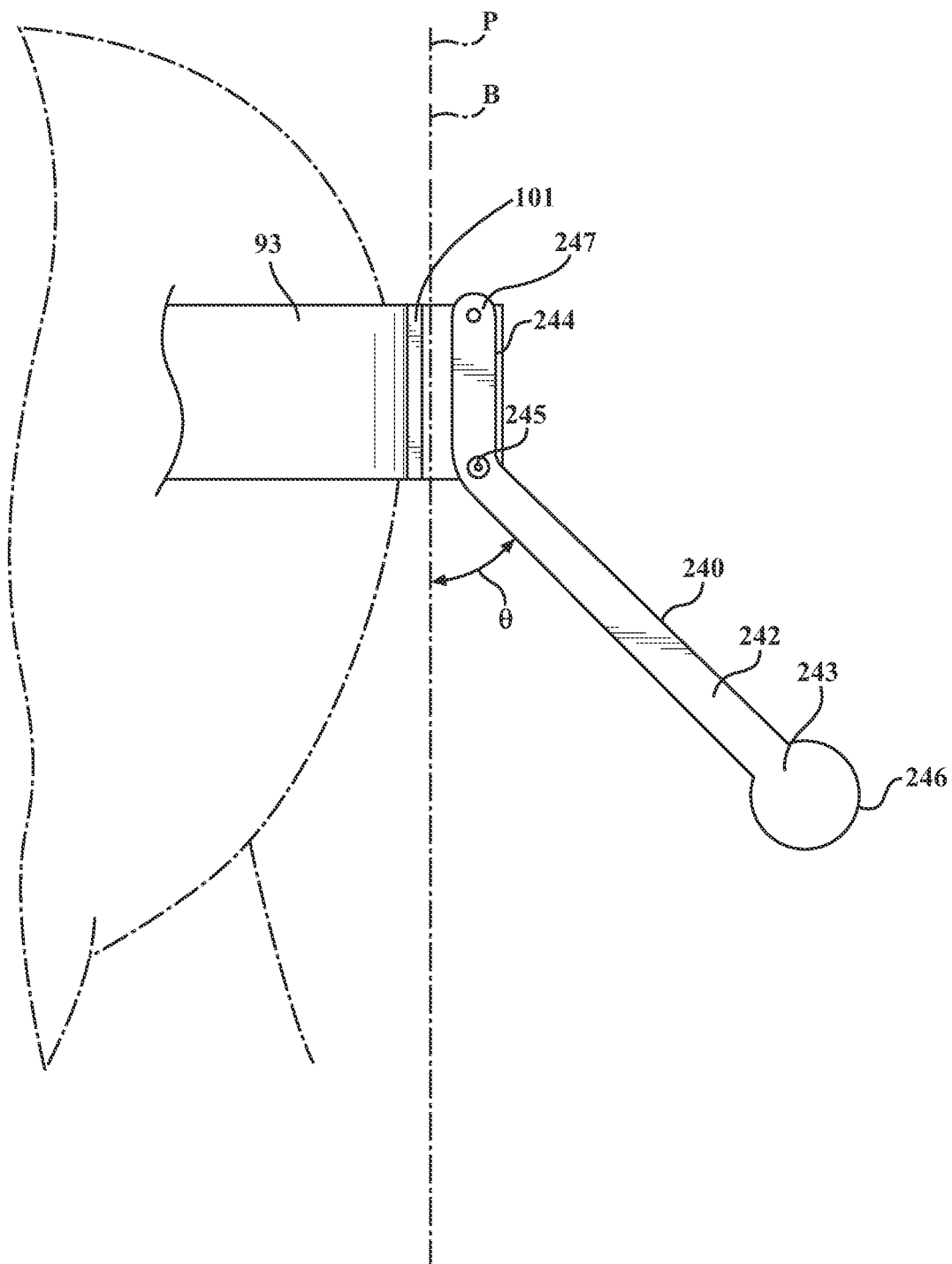
FIG. 19A is a diagram showing a lighting system that comprises a counterbalance system when the head band of the lighting system is in a first angular orientation relative to a plane perpendicular to the earth.
Figure 19B:
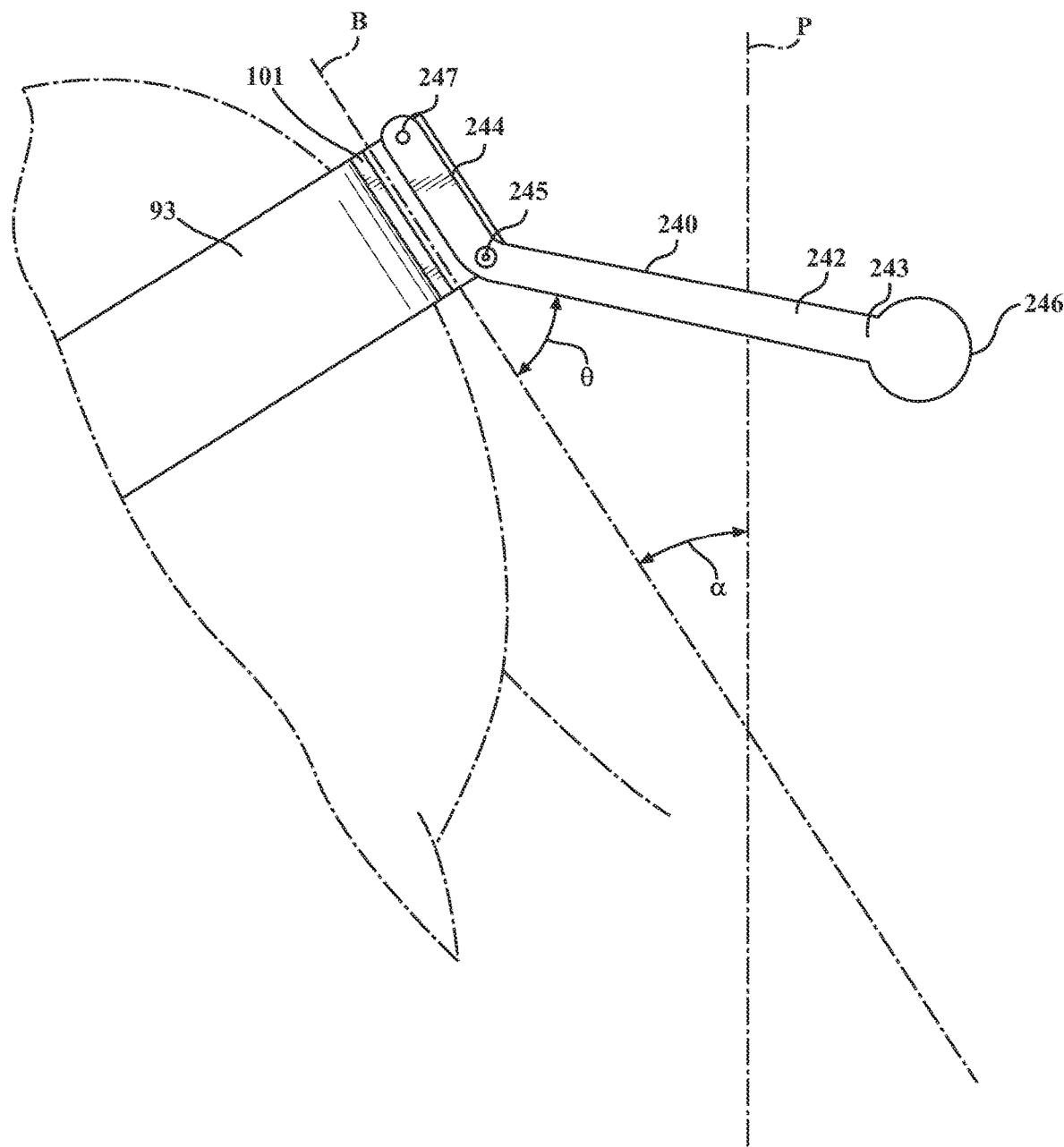
FIG. 19B is a diagram showing the lighting system of FIG. 19A when the head band is in a second angular orientation relative to a plane perpendicular to the earth.

Referring to FIGS. 19A and 19B, a lighting system is depicted which comprises the lighting apparatus 20 (only a portion of which is shown) previously discussed and a counterbalance system 240. Counterbalance system 240 comprises a support 242 and a bracket 244. Bracket 244 is connected to bracket 101 which is attached to head band 93. Counterbalance mass 246 is attached to a distal end 243 of support 242. A proximal end 245 of support 242 is attached to a first end of bracket 244. In certain known lighting systems, a counterbalance mass is attached directly to the head band. However, with increased levering due to the use of support 242, the weight of counterbalance mass 246 may be decreased while still providing the same level of comfort to user. The decrease in weight reduces the likelihood that the head band 93 will slide off the user's head. The reduction in weight of the counterbalance mass also reduces the head band ratchet tightness that is required because of the reduced propensity of the head band 93 to slide off the user's head. In certain preferred examples, the distance of counterbalance mass 246 from head band 93 is user adjustable, as is the weight of counterbalance mass 246. However, in other examples, the distance of the counterbalance mass 246 from head band 93 is fixed.

In preferred examples, counterbalance mass 246 is adjustably repositionable along the length of support 242. In one example, a sliding block that slides along a rail assembly along support 242 length may be provided, and the sliding block may be configured to accommodate small weights that can be added or removed to obtain a desired weight. In certain cases, the weights may comprise pennies or objects of similar size, geometry, and weight. The sliding block may be secured at desired locations along the length of support 242 using a wing nut or other common fastener.

The head band 93 defines a plane "B" that is tangent to the rear-most point of the head band. Support 242 defines an angle θ relative to the plane B that is preferably non-orthogonal. The value of θ is preferably from about 10 degrees to 120 degrees, more preferably from about 20 degrees to about 90 degrees and still more preferably from about 30 degrees to about 60 degrees. The length of support 242 is preferably from about 30 mm to about 120 mm, more preferably from about 50 mm to about 100 mm, and still more preferably from about 70 mm to about 80 mm.

In certain examples, the angle θ is user adjustable. For example, support 242 may be pivotally connected to bracket 244 at a pivot point located at or near proximal end 245. In one implementation, a wing nut or other suitable adjustable fastener may be provided which can be tightened or loosened to securely vary the angle θ at different values as desired by the user.

Values of the mass of counterbalance mass 246 range are less than 1000 grams. Preferred values are from about 50 grams to about 250 grams, and more preferred values are from about 50 grams to about 100 grams. In certain implementations, the total mass of counterbalance mass 246 is adjustable, such as by adding or subtracting individual masses that can be used to provide a total counterbalance mass.

In accordance with one method, a user dons the lighting system of FIGS. 19A and 19B by placing the head band 93 over his or her head and securing the head band ratchet (not shown). The user (or an assistant) may then adjust the position of the counterbalance mass 246 along the length of support 242 and/or pivot support 242 about a pivot point located at or near proximal end 245 until the desired value of θ is reached. The user may then secure the support 242 relative to bracket 244, such as by using a wing nut.

In FIG. 19A the user is standing essentially erect such that the plane B is perpendicular to the Earth. In FIG. 19B the user's head is tilted as would often be the case during a surgical procedure. As a result, plane "B" is oriented at an angle α relative to the plane "P" that is perpendicular to the Earth and to the length axis of support 240. In this orientation, the lighting apparatus 20 may exert a downward force and corresponding torque on the user's spine, and counterbalance system 240 counteracts that force and torque to improve user comfort.

What is claimed is:

1. A personal cooling apparatus, comprising:
    a head band;
    a fan module connected to the head band, wherein the fan module is rotatable about an axis of rotation, and the axis of rotation is movable to a plurality of distances from the head band along a first axis and a plurality of distances from the head band along a second axis;
    an array of fan modules connected to the head band, wherein the array of fan modules includes the fan module.

2. The personal cooling apparatus in accordance of claim 1, wherein the fan module has an adjustable orientation relative to the head band.

3. The personal cooling apparatus of claim 1, wherein the fan module comprises a fan that rotates in a rotational plane, and the rotational plane is adjustable relative to the head band.

4. A personal cooling apparatus, comprising:
    a head band; and
    a fan module integrated into the head band, wherein the head band comprises at least one vent open to atmosphere and at least one internal air passageway in fluid communication with the at least one vent, the at least one internal passageway defines a path for airflow located between the fan module and the at least one vent, the fan module is connected to one end of the internal passageway to direct air through the at least one internal air passageway and out of the at least one vent to the atmosphere.

5. The personal cooling apparatus of claim 4, further comprising a secondary heating or cooling source in fluid communication with the fan module.

6. A cooled lighting apparatus, comprising:
    the personal cooling apparatus of claim 4, and
    a lighting apparatus comprising a hot air exhaust conduit in fluid communication with the at least one internal air passageway, wherein the personal cooling apparatus is operable to draw heated air from the lighting apparatus and exhaust the heated air from the fan module.

7. The cooled lighting apparatus of claim 6, wherein the lighting apparatus comprises:
    a housing;
    a heat sink disposed in the housing, wherein the heat sink has a proximal end and a distal end spaced apart by a length defining a length axis, the heat sink has a recess extending along a portion of the length; and a light emitting diode having a mounting plane, wherein the light emitting diode has a mounting plane located in the recess between the proximal end and the distal end of the heat sink.

8. The cooled lighting apparatus of claim 7, wherein the heat sink has a body located proximally of the recess and a plurality of fins projecting away from the body, wherein the fins in the plurality of fins are spaced apart from one another along the length axis, and a subset of the fins is located between the light emitting diode and the distal end of the heat sink.

9. The cooled lighting apparatus of claim 7, further comprising a convective air flow path through the housing, wherein a portion of the heat sink distal of the light emitting diode mounting plane lies in the convective airflow path.

10. The cooled lighting apparatus of claim 9, wherein the housing comprises at least one air intake vent and at least one air exhaust vent, and the at least one air intake vent, and the at least one air exhaust vent lies in the convective airflow path.

11. The cooled lighting apparatus of claim 10, wherein the heat sink has a body with a frustoconical shape.

12. The cooled lighting apparatus of claim 7, wherein the heat sink has a body located proximally of the recess and a plurality of fins projecting away from the body, wherein the fins in the plurality of fins are spaced apart from one another along the length axis, and a subset of the fins is located between the light emitting diode and the distal end of the heat sink.

13. The cooled lighting apparatus of claim 7, wherein the housing is formed from a thermally insulating material and the heat sink is formed from a thermally conductive material.

14. The cooled lighting apparatus of claim 7, further comprising an an optic located in the housing and distal of the heat sink such that the optic is movable within the housing along the length axis.

15. The cooled lighting apparatus of claim 7, wherein the light emitting diode has a power output of at least about 5 W.

16. The cooled lighting apparatus of claim 7, wherein the heat sink consists essentially of aluminum.

17. The cooled lighting apparatus of claim 7, wherein the heat sink has a thermal conductivity of at least about 150 W/m-° C. at 25° C.

18. A personal cooling apparatus, comprising:
a head band;
a fan module connected to the head band, wherein the fan module is rotatable about an axis of rotation, and the axis of rotation is movable to a plurality of distances from the head band along a first axis and a plurality of distances from the head band along a second axis; and
a plurality of articulating arms, the plurality of articulating arms has a first end connected to the head band and a second end connected to the fan module, a first articulating arm of the plurality of articulating arms includes the first end and is pivotable relative to the head band, and a second articulating arm of the plurality of articulating arms includes the second end and is pivotable relative to the fan module and the head band.

* * * * *